United States Patent
Poulsen

(12) 
(10) Patent No.: US 6,232,122 B1
(45) Date of Patent: May 15, 2001

(54) INHIBITION OF GENE EXPRESSION

(75) Inventor: Peter Poulsen, Copenhagen (DK)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 08/983,440

(22) PCT Filed: Jul. 12, 1996

(86) PCT No.: PCT/EP96/03053

§ 371 Date: Apr. 17, 1998

§ 102(e) Date: Apr. 17, 1998

(87) PCT Pub. No.: WO97/04113

PCT Pub. Date: Feb. 6, 1997

(30) Foreign Application Priority Data

Jul. 14, 1995 (GB) .................................................. 9514437

(51) Int. Cl.[7] .............................. C12N 5/04; C07H 21/04; A01H 1/00

(52) U.S. Cl. ........................ 435/419; 536/23.2; 536/24.1; 800/278

(58) Field of Search ........................... 435/419; 536/23.2, 536/24.1; 800/278

(56) References Cited

U.S. PATENT DOCUMENTS 4,740,463  4/1988  Weinberg et al. ................. 435/172.3

FOREIGN PATENT DOCUMENTS

| WO 92/11375 | 7/1992 | (WO) . |
|---|---|---|
| WO 92/13090 | 8/1992 | (WO) . |
| WO 92/14827 | 9/1992 | (WO) . |
| WO 92/15680 | 9/1992 | (WO) . |
| WO 94/09144 | 4/1994 | (WO) . |
| WO 94/11520 | 5/1994 | (WO) . |
| WO 95/26407 | 10/1995 | (WO) . |

OTHER PUBLICATIONS

Plant Polymeric Carbohydrates, pp. 33–39, Jan. 7, 1993.
Journal of Biological Chemistry, vol. 268, No. 25, pp. 19084–91, 1993.
Plant Molecular Biology, vol. 26, pp. 1759–73, 1994.
Theor. Appl. Genet., vol. 88, pp. 369–375, 1994.
Mol. Gen. Genet., vol. 246, pp. 745–55, 1995.
Theor. Appl. Genet., vol. 86, pp. 665–72, 1993.
Biochem. Genetics, vol. 121, p. 283, 1994.
Plant Physiol., vol. 107, pp. 679–85, 1995.

*Primary Examiner*—Hankyel T. Park
(74) *Attorney, Agent, or Firm*—Frommer Lawrence & Haug LLP; Thomas J. Kowalski

(57) ABSTRACT

A method of inhibiting gene expression in is described. The method, which affects enzymatic activity in a plant, involves expressing in a plant, or a cell, cell line, tissue, or an organ thereof, a nucleotide sequence wherein the nucleotide sequence codes for an intron, or an intron fragment, of an SBE gene in a sense orientation; and wherein the nucleotide sequence does not contain a sequence that is sense to an exon sequence normally associated with the intron.

70 Claims, 17 Drawing Sheets

Figure 2:
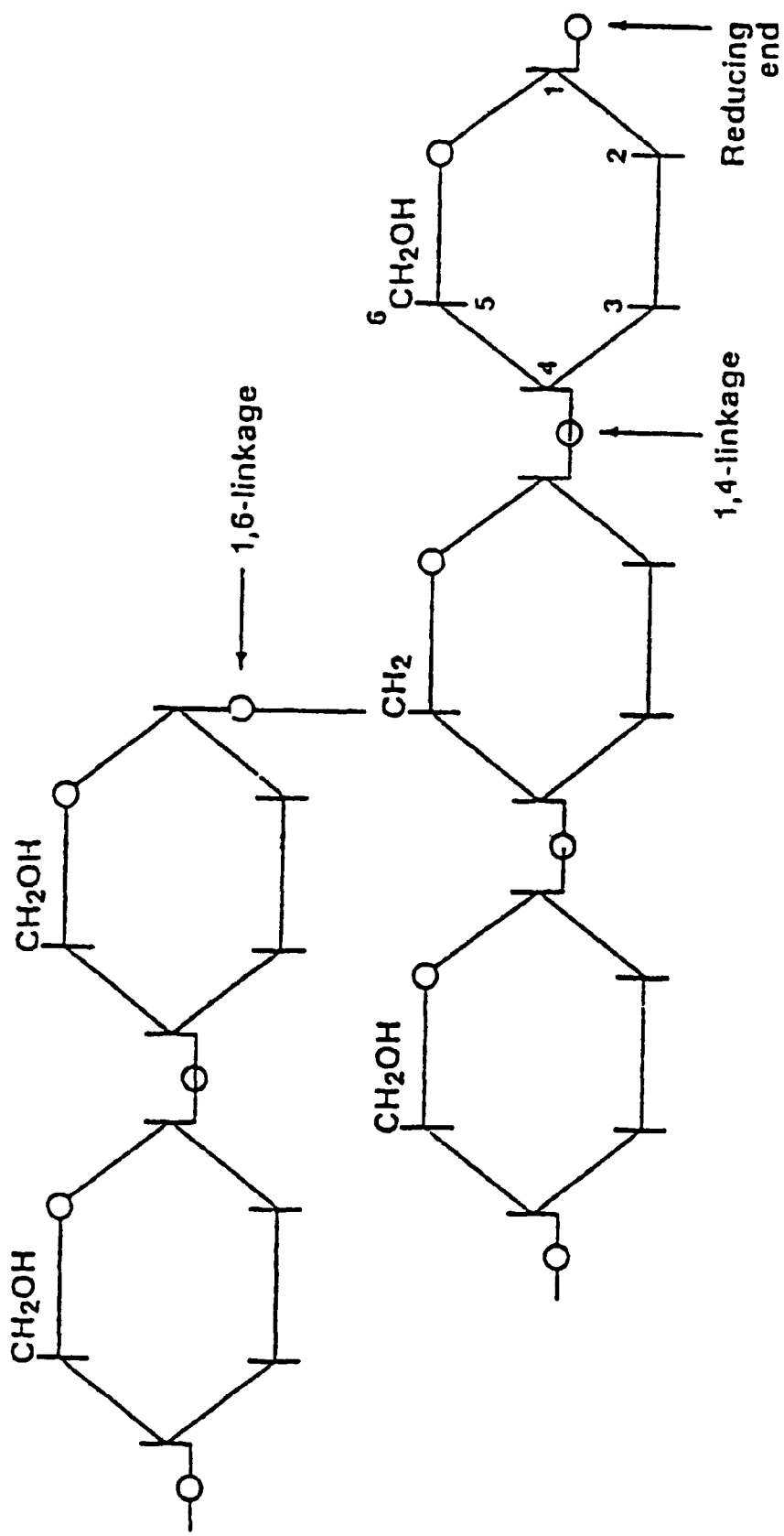

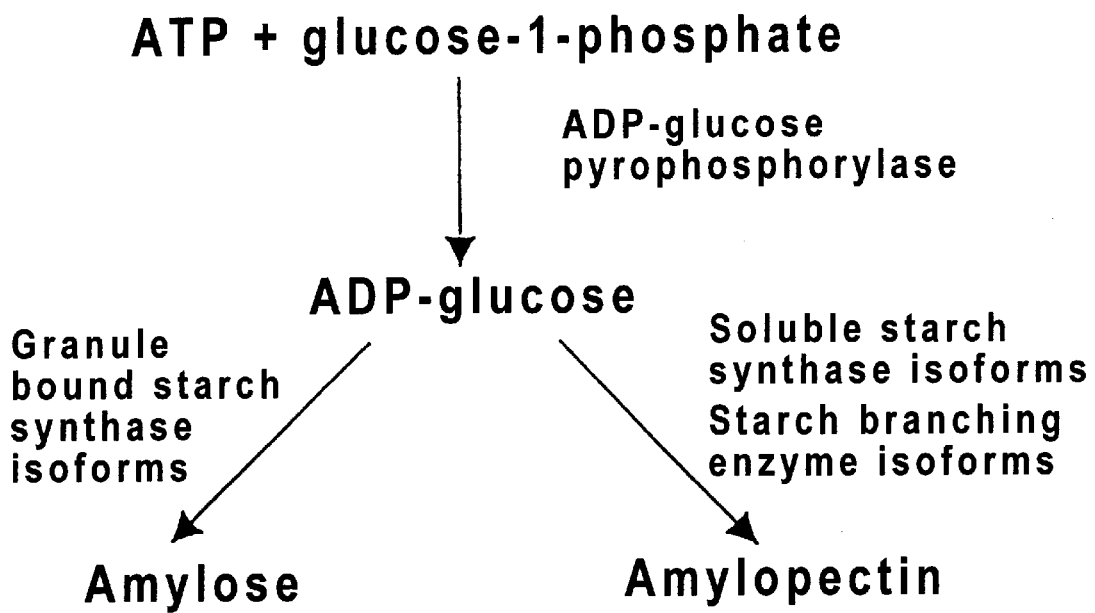
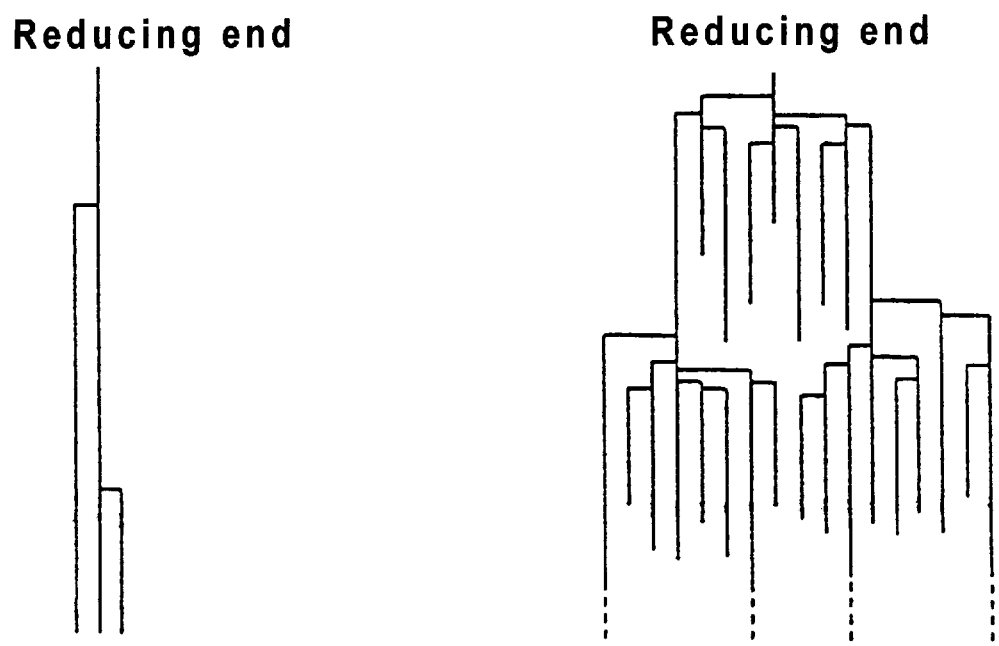
FIG 1

```
              10        20        30        40        50        60
     123456789012345678901234567890123456789012345678901234567890
     ATCATGGCCAATTACTGGTTCAAATGCATTACTTCCTTTCAGATTCTTTCGAGTTCTCAT      60
     GACCGGTCCTACTACAGACGATACTAACCCGTGGAACTGTTGCATCTGCTTCTTAGAACT     120
     CTATGGCTATTTTCGTTAGCTTGGCGTCGGTTTGAACATAGTTTTTGTTTTCAAACTCTT     180
     CATTTACAGTCAAAATGTTGTATGGTTTTTGTTTTCCTCAATGATGTTTACAGTGTTGTG     240
     TTGTCATCTGTACTTTTGCCTATTACTTGTTTTGAGTTACATGTTAAAAAAGTGTTTATT     300
     TTGCCATATTTTGTTCTCTTATTATTATTATCATACATACATTATTACAAGGAAAAGACA     360
     AGTACACAGATCTTAACGTTTATGTTCAATCAACTTTTGGAGGCATTGACAGGTACCACA     420
     AATTTTGAGTTTATGATTAAGTTCAATCTTAGAATATGAATTTAACATCTATTATAGATG     480
     CATAAAAATAGCTAATGATAGAACATTGACATTTGGCAGAGCTTAGGGTATGGTATATCC     540
     AACGTTAATTTAGTAATTTTTGTTACGTACGTATATGAAATATTGAATTAATCACATGAA     600
     CGGTGGATATTATATTATGAGTTGGCATCAGCAAAATCATTGGTGTAGTTGACTGTAGTT     660
     GCAGATTTAATAATAAAATGGTAATTAACGGTCGATATTAAAATAACTCTCATTTCAAGT     720
     GGGATTAGAACTAGTTATTAAAAAAATGTATACTTTAAGTGATTTGATGGCATATAATTT     780
     AAAGTTTTTCATTTCATGCTAAAATTGTTAATTATTGTAATGTAGACTGCGACTGGAATT     840
     ATTATAGTGTAAATTTATGCATTCAGTGTAAAATTAAAGTATTGAACTTGTCTGTTTTAG     900
     AAAATACTTTATACTTTAATATAGGATTTTGTCATGCGAATTTAAATTAATCGATATTGA     960
     ACACGGAATACCAAAATTAAAAAGGATACACATGGCCTTCATATGAACCGTGAACCTTTG    1020
     ATAACGTGGAAGTTCAAAGAAGGTAAAGTTTAAGAATAAACTGACAAATTAATTTCTTTT    1080
     ATTTGGCCCACTACTAAATTTGCTTTACTTTCTAACATGTCAAGTTGTGCCCTCTTAGTT    1140
     GAATGATATTCATTTTTCATCCCATAAGTTCAATTTGATTGTCATACCACCCATGATGTT    1200
     CTGAAAAATGCTTGGCCATTCACAAAGTTTATCTTAGTTCCTATGAACTTTATAAGAAGC    1260
     TTTAATTTGACATGTTATTTATATTAGATGATATAATCCATGACCCAATAGACAAGTGTA    1320
     TTAATATTGTAACTTTGTAATTGAGTGTGTCTACATCTTATTCAATCATTTAAGGTCATT    1380
     AAAATAAATTATTTTTTGACATTCTAAAACTTTAAGCAGAATAAATAGTTTATCAATTAT    1440
     TAAAAACAAAAAACGACTTATTTATAAATCAACAAACAATTTTAGATTGCTCCAACATAT    1500
```

FIG. 8  
FIG. 8A - 8H

FIG. 8A

```
                10        20        30        40        50        60
         1234567890123456789012345678901234567890123456789012345678901234567890
         TTTTCCAAATTAAATGCAGAAAATGCATAATTTTATACTTGATCTTTATAGCTTATTTTT          1560

TTTAGCCTAACCAACGAATATTTGTAAACTCACAACTTGATTAAAAGGGATTTACAACAA          1620

GATATATATAAGTAGTGACAAATCTTGATTTTAAATATTTTAATTTGGAGGTCAAAATTT          1680

TACCATAATCATTTGTATTTATAATTAAATTTTAAATATCTTATTTATACATATCTAGTA          1740

AACTTTTAAATATACGTATATACAAAATATAAAATTATTGGCGTTCATATTAGGTCAATA          1800

AATCCTTAACTATATCTGCCTTACCACTAGGAGAAAGTAAAAAACTCTTTACCAAAAATA          1860

CATGTATTATGTATACAAAAAGTCGATTAGATTACCTAAATAGAAATTGTATAACGAGTA          1920

AGTAAGTAGAAATATAAAAAAACTACAATACTAAAAAAAATATGTTTTACTTCAATTTCG          1980

AAACTAATGGGGTCTGAGTGAAATATTCAGAAAGGGGAGGACTAACAAAAGGGTCATAAT          2040

GTTTTTTTTATAAAAAGCCACTAAAATGAGGAAATCAAGAATCAGAACATACAAGAAGGCA         2100

GCAGCTGAAGCAAAGTACCATAATTTAATCAATGGAAATTAATTTCAAAGTTTTATCAAA          2160
                                             M  E  I  N  F  K  V  L  S  K
         ACCCATTCGAGGATCTTTTCCATCTTTCTCACCTAAAGTTTCTTCAGGGgtaatttttac          2220
          P  I  R  G  S  F  P  S  F  S  P  K  V  S  S  G
         taatttcatgttaatttcaattatttttagcctttgcatttcattttccaatatatctgg          2280 atcatctccttagttttttatttatttttttataatatcaaatatggaagaaaaatgaca          2340 cttgtagagccatatgtaagtatcatgtgacaaatttgcaaggtggttgagtgtataaaa          2400 ttcaaaaattgagagatggagggggggtgggggbaragacaatatttagaaagagtgttc          2460 taggaggttatggaggacacggatgaggggtagaaggttagttaggtatttgagtgttgt          2520 ctggcttatcctttcatactagtagtcgtggaattatttgggtagtttcttgttttgtta          2580 tttgatctttgttattctatttctgtttcttgtacttcgattattgtattatatatctt           2640 gtcgtagttattgttcctcggtaagaatgctctagcatgcttcctttagtgttttatcat          2700 gccttctttatattcgcgttgctttgaaatgcttttactttagccgagggtctattagaa          2760 acaatctctctatctcgtaaggtaggggtaaagtcctcaccacactccacttgtgggatt          2820 acattgtgtttgttgttgtaaatcaattatgtatacataataagtggattttttacaaca          2880 caaatacatggtcaagggcaaagttctgaacacataaagggttcattatatgtccaggga          2940 tatgataaaaattgtttctttgtgaaagttatataagatttgttatggcttttgctggaa          3000
```

FIG. 8
FIG. 8A - 8H

FIG. 8B

```
          10        20        30        40        50        60
 1234567890123456789012345678901234567890123456789012345678901234567890
 acataataagttataatgctgagatagctactgaagtttgttttttctagccttttaaat           3060 gtaccaataatagattccgtatcgaacgagtatgttttgattacctggtcatgatgtttc           3120 tattttttacattttttggtgttgaactgcaattgaaaatgttgtatcctatgagacgg           3180 atagttgagaatgtgttctttgtatggaccttgagaagctcaaacgctactccaataatt          3240 tctatgaattcaaattcagtttatggctaccagtcagtccagaaattaggatatgctgca          3300 tatacttgttcaattatactgtaaaatttcttaagttctcaagatatccatgtaacctcg          3360 agaatttctttgacagGCTTCTAGAAATAAGATATGTTTTCCTTCTCAACATAGTACTGG          3420
                  A  S  R  N  K  I  C  F  P  S  Q  H  S  T  G
 ACTGAAGTTTGGATCTCAGGAACGGTCTTGGGATATTTCTTCCACCCCAAAATCAAGAGT          3480
  L  K  F  G  S  Q  E  R  S  W  D  I  S  S  T  P  K  S  R  V
 TAGAAAAGATGAAAGGgtatgtttgataatttatatggttgcatggatagtatataaata          3540
  R  K  D  E  R
 gttggaaaacttctggactggtgctcatggcatatttgatctgtgcaccgtgtggagatg          3600 tcaaacatgtgttacttcgttccgccaatttataataccttaacttgggaaagacagctc          3660 tttactcctgtgggcatttgttatttgaattacaatctttatgagcatggtgttttcaca         3720 ttatcaacttctttcatgtggtatataacagttttagctccgttaatacctttcttctt          3780 tttgatataaactaactgtggtgcattgcttgcbkkkATGAAGCACAGTTCAGCTATTTC          3840
                                     M  K  H  S  S  A  I  S
 CGCTGTTTTGACCGATGACGACAATTCGACAATGGCACCCCTAGAGGAAGATGTCAAGAC          3900
  A  V  L  T  D  D  D  N  S  T  M  A  P  L  E  E  D  V  K  T
 TGAAAATATTGGCCTCCTAAATTTGGATCCAACTTTGGAACCTTATCTAGATCACTTCAG          3960
  E  N  I  G  L  L  N  L  D  P  T  L  E  P  Y  L  D  H  F  R
 ACACAGAATGAAGAGATATGTGGATCAGAAAATGCTCATTGAAAAATATGAGGGACCCCT          4020
  H  R  M  K  R  Y  V  D  Q  K  M  L  I  E  K  Y  E  G  P  L
 TGAGGAATTTGCTCAAGgtaacagccaaaagttgtgctttaggcagtttgaccttattt           4080
  E  E  F  A  Q  G
 ggaagatgaattgtttatacctactttgactttgctagagaattttgcataccggggagt         4140 aagtagtggctccatttaggtggcacctggccattttttttgatcttttaaaaagctgttt        4200 gattgggtcttcaaaaaagtagacaaggttttttggagaagtgacacacccccggagtgtc       4260 agtggcaaagcaaagattttcactaaggagattcaaaatataaaaaaagtatagacataa         4320 agaagctgaggggattcaacatgtactatacaagcatcaaatatagtcttaaagcaattt         4380 tgtagaaataaagaaagtcttccttctgttgcttcacaatttccttctattatcatgagt         4440 tactctttctgttcgaaatagcttccttaatattaaattcatgatacttttgttgagatt        4500
```

FIG. 8C

```
              10        20        30        40        50        60
    1234567890123456789012345678901234567890123456789012345678901234567890
    tagcagttttttcttgtgtaaactgctctcttttttgcagGTTATTTAAAATTTGGATT            4560
                                            Y  L  K  F  G  F
    CAACAGGGAAGATGGTTGCATAGTCTATCGTGAATGGGCTCCTGCTGCTCAgtaggtcct           4620
     N  R  E  D  G  C  I  V  Y  R  E  W  A  P  A  A  Q
    cgtctactacaaaatagtagtttccatcatcataacagattttcctattaaagcatgatg          4680 ttgcagcatcattggctttcttacatgttctaattgctattaaggttatgcttctaatta          4740 actcatccacaatgcagGGAAGCAGAAGTTATTGGCGATTTCAATGGATGGAACGGTTCT           4800
                      E  A  E  V  I  G  D  F  N  G  W  N  G  S
    AACCACATGATGGAGAAGGACCAGTTTGGTGTTTGGAGTATTAGAATTCCTGATGTTGAC          4860
     N  H  M  M  E  K  D  Q  F  G  V  W  S  I  R  I  P  D  V  D
    AGTAAGCCAGTCATTCCACACAACTCCAGAGTTAAGTTTCGTTTCAAACATGGTAATGGA          4920
     S  K  P  V  I  P  H  N  S  R  V  K  F  R  F  K  H  G  N  G
    GTGTGGGTAGATCGTATCCCTGCTTGGATAAAGTATGCCACTGCAGACGCCACAAAGTTT          4980
     V  W  V  D  R  I  P  A  W  I  K  Y  A  T  A  D  A  T  K  F
    GCAGCACCATATGATGGTGTCTACTGGGACCCACCACCTTCAGAAAGgttttgttattca          5040
     A  A  P  Y  D  G  V  Y  W  D  P  P  P  S  E  R
    taccttgaagctgaattttgaacaccatcatcacaggcatttcgattcatgttcttacta         5100 gtcttgttatgtaagacatttgaaatgcaaaagttaaaataattgtgtctttactaatt           5160 tggacttgatcccatactctttcccttaacaaaatgagtcaattctataagtgcttgaga         5220 acttactacttcagcaattaaacagGTACCACTTCAAATACCCTCGCCCTCCCAAACCCC          5280
                              Y  H  F  K  Y  P  R  P  P  K  P  R
    GAGCCCCACGAATCTATGAAGCACATGTCGGCATGAGCAGCTCTGAGCCACGTGTAAATT          5340
     A  P  R  I  Y  E  A  H  V  G  M  S  S  S  E  P  R  V  N  S
    CGTATCGTGAGTTTGCAGATGATGTTTTACCTCGGATTAAGGCAAATAACTATAATACTG          5400
     R  I  R  E  F  A  D  D  V  L  P  R  I  K  A  N  N  Y  N  T  V
    TCCAGTTGATGGCCATAATGGAACATTCTTACTATGGATCATTTGGATATCATGTTACAA          5460
     Q  L  M  A  I  M  E  H  S  Y  Y  G  S  F  G  Y  H  V  T  N
    ACTTTTTTGCTGTGAGCAGTAGATATGGAAACCCGGAGGACCTAAAGTATCTGATAGATA          5520
     F  F  A  V  S  S  R  Y  G  N  P  E  D  L  K  Y  L  I  D  K
    AAGCACATAGCTTGGGTTTACAGGTTCTGGTGGATGTAGTTCACAGTCATGCAAGCAATA          5580
     A  H  S  L  G  L  Q  V  L  V  D  V  V  H  S  H  A  S  N  N
    ATGTCACTGATGGCCTCAATGGCTTTGATATTGGCCAAGGTTCTCAAGAATCCTACTTTC          5640
     V  T  D  G  L  N  G  F  D  I  G  Q  G  S  Q  E  S  Y  F  H
    ATGCTGGAGAGCGAGGGTACCATAAGTTGTGGGATAGCAGGCTGTTCAACTATGCCAATT          5700
     A  G  E  R  G  Y  H  K  L  W  D  S  R  L  F  N  Y  A  N  W
    GGGAGGTTCTTCGTTTCCTTCTTTCCAACTTGAGGTGGTGGCTAGAAGAGTATAACTTTG          5760
     E  V  L  R  F  L  L  S  N  L  R  W  W  L  E  E  Y  N  F  D
    ACGGATTTCGATTTGATGGAATAACTTCTATGCTGTATGTTCATCATGGAATCAATATGG          5820
     G  F  R  F  D  G  I  T  S  M  L  Y  V  H  H  G  I  N  M  G
    GATTTACAGGAAACTATAATGAGTATTTCAGCGAGGCTACAGATGTTGATGCTGTGGTCT          5880
     F  T  G  N  Y  N  E  Y  F  S  E  A  T  D  V  D  A  V  V  Y
    ATTTAATGTTGGCCAATAATCTGATTCACAAGATTTTCCCAGATGCAACTGTTATTGCCG          5940
     L  M  L  A  N  N  L  I  H  K  I  F  P  D  A  T  V  I  A  E
    AAGATGTTTCTGGTATGCCGGGCCTTGGCCGGCCTGTTTCTGAGGGAGGAATTGGTTTTG          6000
     D  V  S  G  M  P  G  L  G  R  P  V  S  E  G  G  I  G  F  V
```

FIG. 8
FIG. 8A - 8H  FIG. 8D

```
                10        20        30        40        50        60
       1234567890123456789012345678901234567890123456789012345678901234567890
       TTTACCGCCTGGCAATGGCAATCCCAGATAAGTGGATAGATTATTTAAAGAATAAGAATG           6060
         Y  R  L  A  M  A  I  P  D  K  W  I  D  Y  L  K  N  K  N  D
       ATGAAGATTGGTCCATGAAGGAAGTAACATCGAGTTTGACAAATAGGAGATATACAGAGA           6120
         E  D  W  S  M  K  E  V  T  S  S  L  T  N  R  R  Y  T  E  K
       AGTGTATAGCATATGCGGAGACCCATGATCAGgtattttaaatttatttctacaactaaa           6180
         C  I  A  Y  A  E  T  H  D  Q
       taattctcagaacaattgttagatagaatccaaatatatacgtcctgaaagtataaaagt           6240 acttattttcgccatgggccttcagaatattggtagccgctgaatatcatgataagttat           6300 ttatccagtgacatttttatgttcactcctattatgtctgctggatacagTCTATTGTTG           6360
                                                         S  I  V  G
       GTGACAAGACCATTGCATTTCTCCTAATGGACAAAGAGATGTATTCTGGCATGTCTTGCT           6420
         D  K  T  I  A  F  L  L  M  D  K  E  M  Y  S  G  M  S  C  L
       TGACAGATGCTTCTCCTGTTGTTGATCGAGGAATTGCGCTTCACAAGgtttgtctgtttc           6480
         T  D  A  S  P  V  V  D  R  G  I  A  L  H  K
       tattgcattttaaggttcatataggttagccacggaaaatctcactctttgtgaggtaac           6540 cagggttctgatggattattcaatttttctcgtttatcatttgtttattcttttcatgcat           6600 tgtgtttcttttttcaatatccctcttattggaggtaattttttctcatctattcactttt           6660 agcttctaaccacagATGATCCATTTTTTTCACAATGGCCTTGGGAGGAGAGGGGTACCTC           6720
                       M  I  H  F  F  T  M  A  L  G  G  E  G  Y  L
       AATTTCATGGGTAACGAGgtatgtcttacatctttagatatttgtgataattacaatta           6780
         N  F  M  G  N  E
       gtttggcttacttgaacaagattcattcctcaaaatgacctgaactgttgaacatcaaag           6840 gggttgaaacatagaggaaaacaacatgatgaatgtttccattgtctagggatttctatt           6900 atgttgctgagaacaaatgtcatcttaaaaaaaacattgtttacttttttgtagtataga           6960 agattactgtatagagtttgcaagtgtgtctgttttggagtaattgtgaaatgtttgatg           7020 aacttgtacagTTTGGCCATCCTGAGTGGATTGACTTCCCTAGAGAGGGCAATAATTGGA           7080
                    F  G  H  P  E  W  I  D  F  P  R  E  G  N  N  W  S
       GTTATGACAAATGTAGACGCCAGTGGAACCTCGCGGATAGCGAACACTTGAGATACAAGg           7140
         Y  D  K  C  R  R  Q  W  N  L  A  D  S  E  H  L  R  Y  K
       ttcaagtattttgaatcgcagcttgttaaataatctagtaattttagattgcttacttg           7200 gaagtctacttggttctggggatgatagctcatttcatcttgttctacttatttccaac           7260 cgaatttctgattttgtttcgagatccaagtattagattcatttacacttattaccgcc           7320 tcatttctaccactaaggccttgatgagcagcttaagttgattctttgaagctatagttt           7380 caggctaccaatccacagcctgctatatttgttggatacttacctttctttacaatgaa           7440 gtgatactaattgaaatggtctaaatctgatatctatatttctccgtctttcctcccct           7500
```

| FIG. 8 | FIG. 8E |
|--------|---------|
| FIG. 8A - 8H | |

```
                    10        20        30        40        50        60
           1234567890123456789012345678901234567890123456789012345678901234567890
           catgatgaaatgcagTTTATGAATGCATTTGATAGAGCTATGAATTCGCTCGATGAAAAG            7560
                          F  M  N  A  F  D  R  A  M  N  S  L  D  E  K
           TTCTCATTCCTCGCATCAGGAAAACAGATAGTAAGCAGCATGGATGATGATAATAAGgta            7620
            F  S  F  L  A  S  G  K  Q  I  V  S  S  M  D  D  D  N  K
           aaatcatctaaagttgaaagtgttgggtttatgaagtgctttaattctatccaaggacaa            7680 gtagaaaccttttaccttccatttcttgatgatggatttcatattatttaatccaatag             7740 ctggtcaaattcggtaatagctgtactgattagttacttcactttgcagGTTGTTGTGTT            7800
                                                             V  V  V  F
           TGAACGTGGTGACCTGGTATTTGTATTCAACTTCCACCCAAAGAACACATACGAAGGgta            7860
            E  R  G  D  L  V  F  V  F  N  F  H  P  K  N  T  Y  E  G
           tatatgttttacttatccatgaaattattgctctgcttgtttttaatgtactgaacaagt            7920 tttatggagaagtaactgaaacaaatcattttcacattgtctaatttaactcttttttct            7980 gatcctcgcatgacgaaaacagGTATAAAGTTGGATGTGACTTGCCAGGGAAGTACAGAG            8040
                                  Y  K  V  G  C  D  L  P  G  K  Y  R  V
           TTGCACTGGACAGTGATGCTTGGGAATTTGGTGGCCATGGAAGAgtaaggatttgcttga            8100
            A  L  D  S  D  A  W  E  F  G  G  H  G  R
           ataactttgataataagataacagatgtagggtacagttctctcaccaaaaagaactgt             8160 aattgtctcatccatctttagttgtataagatatccgactgtctgagttcggaagtgttt            8220 gagcctcctgccctcccctgcgttgtttagctaattcaaaaaggagaaaactgtttatt            8280 gatgatctttgtcttcatgctgacatacaatctgttctcatgacagACTGGTCATGATGT           8340
                                                            T  G  H  D  V
           TGACCATTTCACATCACCAGAAGGAATACCTGGAGTTCCAGAAACAAATTTCAATGGTCG            8400
            D  H  F  T  S  P  E  G  I  P  G  V  P  E  T  N  F  N  G  R
           TCCAAAATTCCTTCAAAGTGCTGTCTCCTGCGCGAACATGTGTGgtacagttcttgccgtg           8460
            P  N  S  F  K  V  L  S  P  A  R  T  C  V
           tgacctccctttttattgtggttttgttcatagttatttgaatgcgatagaagttaacta            8520 ttgattaccgccacaatcgccagttaagtcctctgaactactaatttgaaaggtaggaat           8580 agccgtaataaggtctacttttggcatcttactgttacaaaacaaaaggatgccaaaaaa           8640 attcttctctatcctctttttccctaaaccagtgcatgtagcttgcacctgcataaactt            8700 aggtaaatgatcaaaaatgaagttgatgggaacttaaaaccgccctgaagtaaagctagg           8760 aatagtcatataatgtccacctttggtgtctgcgctaacatcaacaacaacatacctcgt           8820 gtagtcccacaaagtggtttcaggggagggtagagtgtatgcaaaacttactcctatct            8880 cagaggtagagaggatttttttcaatagacccttggctcaagaaaaaaagtccaaaaagaa         8940 gtaacagaagtgaaagcaacatgtgtagctaaagcgacccaacttgtttgggactgaagt           9000
```

FIG. 8  
FIG. 8A - 8H  FIG. 8F

```
               10        20        30        40        50        60
      1234567890123456789012345678901234567890123456789012345678901234567890
      agttgttgttgttgaaacagtgcatgtagatgaacacatgtcagaaaatggacaacacag             9060 ttattttgtgcaagtcaaaaaaatgtactactatttctttgtgcagctttatgtatagaa             9120 aagttaaataactaatgaattttgctagcagaaaaatagcttggagagaaattttttata             9180 ttgaactaagctaactatattcatctttcttttgcttcttcttctccttgtttgtgaag              9240

GCTTATTACAGAGTTGATGAACGCATGTCAGAAACTGAAGATTACCAGACAGACATTTGT             9300
       A   Y   Y   R   V   D   E   R   M   S   E   T   E   D   Y   Q   T   D   I   C
      AGTGAGCTACTACCAACAGCCAATATCGAGGAGAGTGACGAGAAACTTAAAGATTCGTTA             9360
       S   E   L   L   P   T   A   N   I   E   E   S   D   E   K   L   K   D   S   L
      TCTACAAATATCAGTAACATTGACGAACGCATGTCAGAAACTGAAGTTTACCAGACAGAC             9420
       S   T   N   I   S   N   I   D   E   R   M   S   E   T   E   V   Y   Q   T   D
      ATTTCTAGTGAGCTACTACCAACAGCCAATATTGAGGAGAGTGACGAGAAACTTAAAGAT             9480
       I   S   S   E   L   L   P   T   A   N   I   E   E   S   D   E   K   L   K   D
      TCGTTATCTACAAATATCAGTAACATTGATCAGACTGTTGTAGTTTCTGTTGAGGAGAGA             9540
       S   L   S   T   N   I   S   N   I   D   Q   T   V   V   V   S   V   E   E   R
      GACAAGGAACTTAAAGATTCACCGTCTGTAAGCATCATTAGTGATGTTGTTCCAGCTGAA             9600
       D   K   E   L   K   D   S   P   S   V   S   I   I   S   D   V   V   P   A   E
      TGGGATGATTCAGATGCAAACGTCTGGGGTGAGGACTAGTCAGATGATTGATCGACCCTT             9660
       W   D   D   S   D   A   N   V   W   G   E   D
      CTACCGATTGGTGATCGCTATCCTTGCTCTCTGAGAAATAGGTGAGGCGAAACAAAAAAT             9720

AATTTGCATGATAAAAAGTCTGATTTTATGATCGCTATCCTCGCTCTCTGAGAAAGAAGC             9780

GAAACAAAGGCGACTCCTGGACTCGAATCTATAAGATAACAAAGGCGACTCCTGGGACTC             9840

GAATCTATAAGATAACAAAGGCAATTCCAAGACTTGAATCTATAAAAAATTTAGTTAAGA             9900

ATGATTAACGTCCGATCCTAATTCGAATCGAGGCATCTTACCACTCCATTGATAATTATA             9960

TAAGTCAATAAGTCATATAAWAGTATTAAAAACTAAATTGACTTGATCGGTCTATCAAAA             10020

ATMAGATMAAATTGTGTTCATATGTAACATTTTTGTTGTCACAATTAGCTTAATTACATC             10080

TTTCATGTGCAATAACAAAGAAATGATAGGAATTTAGAGATTCCAATTTTTTTGTTGCCA             10140

CAATTAACTTAATTACATCTTTCATTTGCAATAACAAAGAAATGATAGGAATTTAGAGAT             10200

CCAGTGTCAATACACAACCTAGGCCAACATCGAAAGCATAACTGTAAACTCATGCATGAA             10260

GAAATCAGTCGTAAAAATGAATAAATGCGACATAAAAACAAATTGCATGTATCATTAATG             10320

TGACTTAACTACAAGTAAAAATAAATTTAACAAATGTAACTTAACTACAAGTAAAAATAA             10380

ATTGCTTCTATCATTAACAAACAAACAGAATTAAAAAGAAAAAAACATACTAAATCTTAC             10440

CGTCATTCGATAAAAAAAAATACCAAATTCATAATGCAAGGAAAACGAAACGCGTCCTGA             10500
```

FIG. 8
FIG. 8A - 8H    FIG. 8G

```
          10        20        30        40        50        60
 123456789012345678901234567890123456789012345678901234567890
TCGGGTATCAACGATGAAATGGACCAGTTGGATCGACTGCCTGCACAACGTTAGGTATGC   10560

CAAAAAAAAGAACACGATCCTTTGCACCCGTTCGATGATTATCAGTATGTTCACAAAAAA   10620

AACTTAAGTTCATCCCAGTGTACAACAGCCCCAACATCTGCCCCAAGTAACAAAAAACAA   10680

CCAATTTATCTTATTCTTATCTGCCACAAAATAATCGGTTTCACACTATTCTCTTGTTAT   10740

ACAAAATTGACAAGTAGGAAGGAGAGGAGTCATCCAAATAAACGGTGCACGTTCTTTGAG   10800

AAAAGTCTTATTTTTCGTAAGATCCAATTTCAACAAACTTTTCTTCAAGTCAAAATTCCT   10860

GATAGTGTATCTCCTCTCGACGACCTCTTGCATTGAACGATCTCCGCTTATCATGAAAAG   10920

TTGCTTGGATAACAAGTATTGCAAGGGGGGACAGTAGCTATTAAGTTAGTCGGCCCAAG   10980

GAAATGGAGGAGTGATAGTCTCGAATATTATTCACCTCTTTAGCATTACCCGGTCTGGCT   11040

TTAAGGAGTTACGTCTTTTACGCTCGCCAATTTCTTTTTTTAGAATGGTTGGTGTCAAAA   11100

TCGCGAGTTGTGGAAGGTTCAAGTTACTCGATTCGTGATTTTCAAGTATGAGTGGTGAGA   11160

GAGATTCGATATTTTCACGAGGTGTATTCGAGGTCTAGTAGAACGAAGGGTGTCACTAAT   11220

GAAAGTTTCAAGAGTTCATCATCATCTTCTTCTAGTAGATTTTCGCTTTCAAATGAGTAT   11280

GAAAATTCTTCCTCTTTTCTATTGATTTTCTTCATTGTTTTCTTCATTGTTGTGGTTGTT   11340

ATTGAAAAGAAAGAAAATTTATAACAGAAAAAGATGTCAAAAAAAAGGTAAAATGAAAGA   11400

GTATCATATACTTAAAGAGTTGCGTAGAGATAAGTCAAAAGAAACAGAATTATAGTAATT   11460

TCAGCTAAGTTAGAATTC                                             11478
```

FIG. 8
FIG. 8A - 8H

FIG. 8H

INHIBITION OF GENE EXPRESSION

The present invention relates to a method of inhibiting gene expression, particularly inhibiting gene expression in a plant. The present invention also relates to a nucleotide sequence useful in the method. In addition, the present invention relates to a promoter that is useful for expressing the nucleotide sequence.

Starch is one of the main storage carbohydrates in plants, especially higher plants. The structure of starch consists of amylose and amylopectin. Amylose consists essentially of straight chains of α-1-4-linked glycosyl residues. Amylopectin comprises chains of α-1-4-linked glycosyl residues with some α-1-6 branches. The branched nature of amylopectin is accomplished by the action of inter alia an enzyme commonly known as the starch branching enzyme ("SBE"). SBE catalyses the formation of branch points in the amylopectin molecule by adding α-1,4 glucans through α-1,6-glucosidic branching linkages. The biosynthesis of amylose and amylopectin is schematically shown in FIG. 1, whereas the α-1-4-links and the α-1-6 links are shown in FIG. 2.

It is known that starch is an important raw material. Starch is widely used in the food, paper, and chemical industries. However, a large fraction of the starches used in these industrial applications are post-harvest modified by chemical, physical or enzymatic methods in order to obtain starches with certain required functional properties.

Within the past few years it has become desirable to make genetically modified plants which could be capable of producing modified starches which could be the same as the post-harvest modified starches. It is also known that it may be possible to prepare such genetically modified plants by expression of antisense nucleotide coding sequences. In this regard, June Bourque provides a detailed summary of antisense strategies for the genetic manipulations in plants (Bourque 1995 Plant Science 105 pp 125–149).

Whilst it is known that enzymatic activity can be affected by expression of particular nucleotide sequences (for example see the teachings of Finnegan and McElroy [1994] Biotechnology 12 883–888; and Matzke and Matzke [1995] TIG 11 1–3) there is still a need for a method that can more reliably and/or more efficiently and/or more specifically affect enzymatic activity.

According to a first aspect of the present invention there is provided a method of affecting enzymatic activity in a plant (or a cell, a tissue or an organ thereof) comprising expressing in the plant (or a cell, a tissue or an organ thereof) a nucleotide sequence wherein the nucleotide sequence partially or completely codes (is) an intron in a sense orientation; and wherein the nucleotide sequence does not contain a sequence that is a sense exon sequence normally associated with the intron.

According to a second aspect of the present invention there is provided a method of affecting enzymatic activity in a starch producing organism (or a cell, a tissue or an organ thereof) comprising expressing in the starch producing organism (or a cell, a tissue or an organ thereof) a nucleotide sequence wherein the nucleotide sequence codes, partially or completely, for an intron in a sense orientation; wherein the nucleotide sequence does not contain a sequence that is sense to an exon sequence normally associated with the intron; and wherein starch branching enzyme activity is affected and/or the levels of amylopectin are affected and/or the composition of starch is changed.

According to a third aspect of the present invention there is provided a sequence comprising the nucleotide sequence shown as any one of SEQ.I.D. No. 1 to SEQ.I.D. No. 13 or a variant, derivative or homologue thereof.

According to a fourth aspect of the present invention there is provided a promoter comprising the sequence shown as SEQ.I.D. No. 14 or a variant, derivative or homologue thereof.

According to a fifth aspect of the present invention there is provided a construct capable of comprising or expressing the present invention.

According to a sixth aspect of the present invention there is provided a vector comprising or expressing the present invention.

According to a seventh aspect of the present invention there is provided a cell, tissue or organ comprising or expressing the present invention.

According to an eighth aspect of the present invention there is provided a transgenic starch producing organism comprising or expressing the present invention. According to a ninth aspect of the present invention there is provided a starch obtained from the present invention.

According to a tenth aspect of the present invention there is provided pBEA11 (NCIMB 40754). According to an eleventh aspect of the present invention there is provided a sense nucleotide sequence that is obtainable from λ-SBE 3.2 (NCIMB 40751) or λ-SBE 3.4 (NCIMB 40752) or a variant, derivative or homologue thereof.

A key advantage of the present invention is that it provides a method for preparing modified starches that is not dependent on the need for post-harvest modification of starches. Thus the method of the present invention obviates the need for the use of hazardous chemicals that are normally used in the post-harvest modification of starches.

In addition, the present invention provides inter alia genetically modified plants which are capable of producing modified and/or novel and/or improved starches whose properties would satisfy various industrial requirements.

Thus, the present invention provides a method of preparing tailor-made starches in plants which could replace the post-harvest modified starches.

Also, the present invention provides a method that enables modified starches to be prepared by a method that can have a more beneficial effect on the environment than the known post-harvest modification methods which are dependent on the use of hazardous chemicals and large quantities of energy.

An other key advantage of the present invention is that it provides a method that may more reliably and/or more efficiently and/or more specifically affect enzymatic activity when compared to the known methods of affecting enzymatic activity. With regard to this advantage of the present invention it is to be noted that there is some degree of homology between coding regions of SBEs. However, there is little or no homology with the intron sequences of SBEs. Thus, sense intron expression provides a mechanism to affect selectively the expression of a particular SBE. This advantageous aspect could be used, for example, to reduce or eliminate a particular SBE enzyme and replace that enzyme with another enzyme which can be another branching enzyme or even a recombinant version of the affected enzyme or even a hybrid enzyme which could for example comprise part of a SBE enzyme from one source and at least a part of another SBE enzyme from another source. This particular feature of the present invention is covered by the combination aspect of the present invention which is discussed in more detail later.

Thus the present invention provides a mechanism for selectively affecting SBE activity. This is in contrast to the prior art methods which are dependent on the use of for example antisense exon expression whereby it would not be possible to introduce new SBE activity without affecting that activity as well.

Preferably with the first aspect of the present invention starch branching enzyme activity is affected and/or wherein the levels of amylopectin are affected and/or the composition of starch is changed.

Preferably with the first or second aspect of the present invention the nucleotide sequence does not contain a sequence that is sense to an exon sequence.

Preferably with the fourth aspect of the present invention the promoter is in combination with a gene of interest ("GOI").

Preferably the enzymatic activity is reduced or eliminated.

Preferably the nucleotide sequence codes for at least substantially all of at least one intron in a sense orientation.

Preferably the nucleotide sequence codes, partially or completely, for two or more introns and wherein each intron is in a sense orientation.

Preferably the nucleotide sequence comprises at least 350 nucleotides (e.g. 350 bp), more preferably at least 500 nucleotides (e.g. 500 bp).

Preferably the nucleotide sequence comprises the sequence shown as any one of SEQ. I.D. No. 1 to SEQ.I.D. No. 13 or a variant, derivative or homologue thereof, including combinations thereof.

Preferably the nucleotide sequence is expressed by a promoter having a sequence shown as SEQ. I.D. No. 14 or a variant, derivative or homologue thereof.

Preferably the transgenic starch producing organism is a plant.

A preferred aspect of the present invention therefore relates to a method of affecting enzymatic activity in a plant (or a cell, a tissue or an organ thereof) comprising expressing in the plant (or a cell, a tissue or an organ thereof) a nucleotide sequence wherein the nucleotide sequence codes, partially or completely, for an intron in a sense orientation; wherein the nucleotide sequence does not contain a sequence that is sense to an exon sequence normally associated with the intron; and wherein starch branching enzyme activity is affected and/or the levels of amylopectin are affected and/or the composition of starch is changed.

A more preferred aspect of the present invention therefore relates to a method of affecting enzymatic activity in a plant (or a cell, a tissue or an organ thereof) comprising expressing in the plant (or a cell, a tissue or an organ thereof) a nucleotide sequence wherein the nucleotide sequence codes, partially or completely, for an intron in a sense orientation; wherein the nucleotide sequence does not contain a sequence that is sense to an exon sequence normally associated with the intron; wherein starch branching enzyme activity is affected and/or the levels of amylopectin are affected and/or the composition of starch is changed; and wherein the nucleotide sequence comprises the sequence shown as any one of SEQ.I.D. No. 1 to SEQ.I.D. No. 13 or a variant, derivative or homologue thereof, including combinations thereof.

The term "nucleotide" in relation to the present invention includes DNA and RNA. Preferably it means DNA, more preferably DNA prepared by use of recombinant DNA techniques.

The term "intron" is used in its normal sense as meaning a segment of nucleotides, usually DNA, that does not encode part or all of an expressed protein or enzyme.

The term "exon" is used in its normal sense as meaning a segment of nucleotides, usually DNA, encoding part or all of an expressed protein or enzyme.

Thus, the term "intron" refers to gene regions that are transcribed into RNA molecules, but which are spliced out of the RNA before the RNA is translated into a protein. In contrast, the term "exon" refers to gene regions that are transcribed into RNA and subsequently translated into proteins.

The terms "variant" or "homologue" or "fragment" in relation to the nucleotide sequence of the present invention include any substitution of, variation of, modification of, replacement of, deletion of or addition of one (or more) nucleic acid from or to the respective nucleotide sequence providing the resultant nucleotide sequence can affect enzyme activity in a plant, or cell or tissue thereof, preferably wherein the resultant nucleotide sequence has at least the same effect as any one of the sense sequences shown as SEQ.I.D. No.s 1–13. In particular, the term "homologue" covers homology with respect to similarity of structure and/or similarity of function providing the resultant nucleotide sequence has the ability to affect enzymatic activity in accordance with the present invention. With respect to sequence homology (i.e. similarity), preferably there is more than 80% homology, more preferably at least 85% homology, more preferably at least 90% homology, even more preferably at least 95% homology, more preferably at least 98% homology. The above terms are also synonymous with allelic variations of the sequences.

Likewise, the terms "variant" or "homologue" or "fragment" in relation to the promoter of the present invention include any substitution of, variation of, modification of, replacement of, deletion of or addition of one (or more) nucleic acid from or to the respective promoter sequence providing the resultant promoter sequence allows expression of a GOI, preferably wherein the resultant promoter sequence has at least the same effect as SEQ.I.D. No. 14. In particular, the term "homologue" covers homology with respect to similarity of structure and/or similarity of function providing the resultant promoter sequence has the ability to allow for expression of a GOI, such as a nucleotide sequence according to the present invention. With respect to sequence homology (i.e. similarity), preferably there is more than 80% homology, more preferably at least 85% homology, more preferably at least 90% homology, even more preferably at least 95% homology, more preferably at least 98% homology. The above terms are also synonymous with allelic variations of the sequences.

The intron sequence of the present invention can be any one or all of the intron sequences of the present invention, including partial sequences thereof, provided that if partial sense sequences are used (i.e. sequences that are not or do not comprise any one or more of the full sequences shown as SEQ.I.D. No. 1–13) the partial sequences affect enzymatic activity. Suitable examples of partial sequences include sequences that are shorter than any one of the full sense sequences shown as SEQ.I.D.No.s 1 to 13 but which comprise nucleotides that are adjacent the respective exon or exons.

With regard to the second aspect of the present invention (i.e. specifically affecting SBE activity), the nucleotide sequences of the present invention may comprise one or more sense or antisense exon sequences of the SBE gene (but not sense exon sequences naturally associated with the intron sequence), including complete or partial sequences thereof, providing the nucleotide sequences can affect SBE activity, preferably wherein the nucleotide sequences reduce or eliminate SBE activity. Preferably, the nucleotide sequence of the second aspect of the present invention does not comprise sense exon sequences.

The term "vector" includes an expression vector and a transformation vector. The term "expression vector" means a construct capable of in vivo or in vitro expression. The term "transformation vector" means a construct capable of being transferred from one species to another—such as from an *E. Coli* plasmid to a fungus or a plant cell, or from an Agrobacterium to a plant cell.

The term "construct"—which is synonymous with terms such as "conjugate", "cassette" and "hybrid"—in relation to the sense nucleotide sequence aspect of the present invention includes the nucleotide sequence according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. The terms do not cover the natural combination of the wild type SBE gene when associated with the wild type SBE gene promoter in their natural environment.

The construct may even contain or express a marker which allows for the selection of the genetic construct in, for example, a plant cell into which it has been transferred. Various markers exist which may be used in, for example, plants—such as mannose. Other examples of markers include those that provide for antibiotic resistance—e.g. resistance to G418, hygromycin, bleomycin, kanamycin and gentamycin.

The construct of the present invention preferably comprises a promoter. The term "promoter" is used in the normal sense of the art, e.g. an RNA polymerase binding site in the Jacob-Monod theory of gene expression. Examples of suitable promoters are those that can direct efficient expression of the nucleotide sequence of the present invention and/or in a specific type of cell. Some examples of tissue specific promoters are disclosed in WO 92/11375.

The promoter could additionally include conserved regions such as a Pribnow Box or a TATA box. The promoters may even contain other sequences to affect (such as to maintain, enhance, decrease) the levels of expression of the nucleotide sequence of the present invention. Suitable examples of such sequences include the Sh1-intron or an ADH intron. Other sequences include inducible elements—such as temperature, chemical, light or stress inducible elements. Also, suitable elements to enhance transcription or translation may be present. An example of the latter element is the TMV 5' leader sequence (see Sleat Gene 217 [1987] 217–225; and Dawson Plant Mol. Biol. 23 [1993] 97).

As mentioned, the construct and/or the vector of the present invention may include a transcriptional initiation region which may provide for regulated or constitutive expression. Any suitable promoter may be used for the transcriptional initiation region, such as a tissue specific promoter. In one aspect, preferably the promoter is the patatin promoter or the E35S promoter. In another aspect, preferably the promoter is the SBE promoter.

If, for example, the organism is a plant then the promoter can be one that affects expression of the nucleotide sequence in any one or more of seed, tuber, stem, sprout, root and leaf tissues, preferably tuber. By way of example, the promoter for the nucleotide sequence of the present invention can be the α-Amy 1 promoter (otherwise known as the Amy 1 promoter, the Amy 637 promoter or the α-Amy 637 promoter) as described in our co-pending UK patent application No. 9421292.5 filed Oct. 21, 1994. Alternatively, the promoter for the nucleotide sequence of the present invention can be the α-Amy 3 promoter (otherwise known as the Amy 3 promoter, the Amy 351 promoter or the α-Amy 351 promoter) as described in our co-pending UK patent application No. 9421286.7 filed Oct. 21, 1994.

The present invention also encompasses the use of a promoter to express a nucleotide sequence according to the present invention, wherein a part of the promoter is inactivated but wherein the promoter can still function as a promoter. Partial inactivation of a promoter in some instances is advantageous. In particular, with the Amy 351 promoter mentioned earlier it is possible to inactivate a part of it so that the partially inactivated promoter expresses the nucleotide sequence of the present invention in a more specific manner such as in just one specific tissue type or organ. The term "inactivated" means partial inactivation in the sense that the expression pattern of the promoter is modified but wherein the partially inactivated promoter still functions as a promoter. However, as mentioned above, the modified promoter is capable of expressing a gene coding for the enzyme of the present invention in at least one (but not all) specific tissue of the original promoter. Examples of partial inactivation include altering the folding pattern of the promoter sequence, or binding species to parts of the nucleotide sequence, so that a part of the nucleotide sequence is not recognised by, for example, RNA polymerase. Another, and preferable, way of partially inactivating the promoter is to truncate it to form fragments thereof. Another way would be to mutate at least a part of the sequence so that the RNA polymerase can not bind to that part or another part. Another modification is to mutate the binding sites for regulatory proteins for example the CreA protein known from filamentous fungi to exert carbon catabolite repression, and thus abolish the catabolite repression of the native promoter.

The construct and/or the vector of the present invention may include a transcriptional termination region.

The nucleotide according to the present invention can be expressed in combination (but not necessarily at the same time) with an additional construct. Thus the present invention also provides a combination of constructs comprising a first construct comprising the nucleotide sequence according to the present invention operatively linked to a first promoter; and a second construct comprising a GOI operatively linked to a second promoter (which need not be the same as the first promoter). With this aspect of the present invention the combination of constructs may be present in the same vector, plasmid, cells, tissue, organ or organism. This aspect of the present invention also covers methods of expressing the same, preferably in specific cells or tissues, such as expression in just a specific cell or tissue, of an organism, typically a plant. With this aspect of the present invention the second construct does not cover the natural combination of the gene coding for an enzyme ordinarily associated with the wild type gene promoter when they are both in their natural environment.

An example of a suitable combination would be a first construct comprising the nucleotide sequence of the present invention and a promoter, such as the promoter of the present invention, and a second construct comprising a promoter, such as the promoter of the present invention, and a GOI wherein the GOI codes for another starch branching enzyme either in sense or antisense orientation.

The above comments relating to the term "construct" for the sense nucleotide aspect of the present invention are equally applicable to the term "construct" for the promoter aspect of the present invention. In this regard, the term includes the promoter according to the present invention directly or indirectly attached to a GOI.

The term "GOI" with reference to the promoter aspect of the present invention or the combination aspect of the present invention means any gene of interest, which need not necessarily code for a protein or an enzyme - as is explained later. A GOI can be any nucleotide sequence that is either foreign or natural to the organism in question, for example a plant.

Typical examples of a GOI include genes encoding for other proteins or enzymes that modify metabolic and catabolic processes. The GOI may code for an agent for introducing or increasing pathogen resistance.

The GOI may even be an antisense construct for modifying the expression of natural transcripts present in the relevant tissues. An example of such a GOI is the nucleotide sequence according to the present invention.

The GOI may even code for a protein that is non-natural to the host organism—e.g. a plant. The GOI may code for a compound that is of benefit to animals or humans. For example, the GOI could code for a pharmaceutically active protein or enzyme such as any one of the therapeutic compounds insulin, interferon, human serum albumin, human growth factor and blood clotting factors. The GOI may even code for a protein giving additional nutritional value to a food or feed or crop. Typical examples include plant proteins that can inhibit the formation of anti-nutritive factors and plant proteins that have a more desirable amino acid composition (e.g. a higher lysine content than a non-transgenic plant). The GOI may even code for an enzyme that can be used in food processing such as xylanases and α-galactosidase. The GOI can be a gene encoding for any one of a pest toxin, an antisense transcript such as that for α-Amylase, a protease or a glucanase. Alternatively, the GOI can be a nucleotide sequence according to the present invention.

The GOI can be the nucleotide sequence coding for the arabinofuranosidase enzyme which is the subject of our co-pending UK patent application 9505479.7. The GOI can be the nucleotide sequence coding for the glucanase enzyme which is the subject of our co-pending UK patent application 9505475.5. The GOI can be the nucleotide sequence coding for the ce-amylase enzyme which is the subject of our co-pending UK patent application 9413439.2. The GOI can be the nucleotide sequence coding for the α-Amylase enzyme which is the subject of our co-pending UK patent application 9421290.9. The GOI can be any of the nucleotide sequences coding for the α-glucan lyase enzyme which are described in our co-pending PCT patent application PCT/EP94/03397.

In one aspect the GOI can even be a nucleotide sequence according to the present invention but when operatively linked to a different promoter.

The GOI could include a sequence that codes for one or more of a xylanase, an arabinase, an acetyl esterase, a rhamnogalacturonase, a glucanase, a pectinase, a branching enzyme or another carbohydrate modifying enzyme or proteinase. Alternatively, the GOI may be a sequence that is antisense to any of those sequences.

As mentioned above, the present invention provides a mechanism for selectively affecting a particular enzymatic activity In an important application of the present invention it is now possible to reduce or eliminate expression of a genomic nucleotide sequence coding for a genomic protein or enzyme by expressing a sense intron construct for that particular genomic protein or enzyme and (e.g. at the same time) expressing a recombinant version of that enzyme or protein—in other words the GOI is a recombinant nucleotide sequence coding for the genomic enzyme or protein. This application allows expression of desired recombinant enzymes and proteins in the absence of (or reduced levels of) respective genomic enzymes and proteins. Thus the desired recombinant enzymes and proteins can be easily separated and purified from the host organism. This particular aspect of the present invention is very advantageous over the prior art methods which, for example, rely on the use of anti-sense exon expression which methods also affect expression of the recombinant enzyme.

Thus, a further aspect of the present invention relates to a method of expressing a recombinant protein or enzyme in a host organism comprising expressing a nucleotide sequence coding for the recombinant protein or enzyme; and expressing a further nucleotide sequence wherein the further nucleotide sequence codes, partially or completely, for an intron in a sense orientation; wherein the intron is an intron normally associated with the genomic gene encoding a protein or an enzyme corresponding to the recombinant protein or enzyme; and wherein the further nucleotide sequence does not contain a sequence that is sense to an exon sequence normally associated with the intron. Additional aspects cover the combination of those nucleotide sequences including their incorporation in constructs, vectors, cells, tissues and transgenic organisms.

Therefore the present invention also relates to a combination of nucleotide sequences comprising a first nucleotide sequence coding for a recombinant enzyme; and a second nucleotide sequence which corresponds to an intron in a sense orientation; wherein the intron is an intron that is associated with a genomic gene encoding the enzyme corresponding to the recombinant enzyme; and wherein the second nucleotide sequence does not contain a sequence that is sense to an exon sequence normally associated with the intron.

The GOI may even code for one or more introns but in an antisense orientation, such as any one or more of the antisense intron sequences presented in the attached sequence listings. For example, the present invention also covers the expression of for example a sense intron (e.g. SEQ.I.D.No. 1) in combination with for example an anti-sense sense intron which preferably is not complementary to the sense intron sequence (e.g. SEQ.I.D.No. 16).

The terms "cell", "tissue" and "organ" include cell, tissue and organ per se and when within an organism.

The term "organism" in relation to the present invention includes any organism that could comprise the nucleotide sequence according to the present invention and/or wherein the nucleotide sequence according to the present invention can be expressed when present in the organism. Preferably the organism is a starch producing organism such as any one of a plant, algae, fungi, yeast and bacteria, as well as cell lines thereof. Preferably the organism is a plant.

The term "starch producing organism" includes any organism that can biosynthesise starch. Preferably, the starch producing organism is a plant.

The term "plant" as used herein includes any suitable angiosperm, gymnosperm, monocotyledon and dicotyledon. Typical examples of suitable plants include vegetables such as potatoes; cereals such as wheat, maize, and barley; fruit; trees; flowers; and other plant crops. Preferably, the term means "potato".

The term transgenic organism in relation to the present invention includes any organism that comprises the nucleotide sequence according to the present invention and/or products obtained therefrom, and/or wherein the nucleotide sequence according to the present invention can be expressed within the organism. Preferably the nucleotide sequence of the present invention is incorporated in the genome of the organism. Preferably the transgenic organism is a plant, more preferably a potato.

To prepare the host organism one can use prokaryotic or eukaryotic organisms. Examples of suitable prokaryotic hosts include *E. coli* and *Bacillus subtilis*. Teachings on the transformation of prokaryotic hosts is well documented in the art, for example see Sambrook et al (Sambrook et al. in Molecular Cloning: A Laboratory Manual, 2nd edition, 1989, Cold Spring Harbor Laboratory Press).

Even though the enzyme according to the present invention and the nucleotide sequence coding for same are not disclosed in EP-B-0470145 and CA-A-2006454, those two documents do provide some useful background commentary on the types of techniques that may be employed to prepare transgenic plants according to the present invention. Some of these background teachings are now included in the following commentary.

The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27).

Thus, in one aspect, the present invention relates to a vector system which carries a nucleotide sequence or construct according to the present invention and which is capable of introducing the nucleotide sequence or construct into the genome of an organism, such as a plant.

The vector system may comprise one vector, but it can comprise two vectors. In the case of two vectors, the vector system is normally referred to as a binary vector system. Binary vector systems are described in further detail in Gynheung An et al. (1980), Binary Vectors, *Plant Molecular Biology Manual* A3, 1–19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* An et al. (1986), *Plant Physiol.* 81, 301–305 and Butcher D. N. et al. (1980), *Tissue Culture Methods for Plant Pathologists*, eds.: D. S. Ingrams and J. P. Helgeson, 203–208. Several different Ti and Ri plasmids have been constructed which are suitable for the construction of the plant or plant cell constructs described above. A non-limiting example of such a Ti plasmid is pGV3850.

The nucleotide sequence or construct of the present invention should preferably be inserted into the Ti-plasmid between the terminal sequences of the T-DNA or adjacent a T-DNA sequence so as to avoid disruption of the sequences immediately surrounding the T-DNA borders, as at least one of these regions appears to be essential for insertion of modified T-DNA into the plant genome.

As will be understood from the above explanation, if the organism is a plant the vector system of the present invention is preferably one which contains the sequences necessary to infect the plant (e.g. the vir region) and at least one border part of a T-DNA sequence, the border part being located on the same vector as the genetic construct.

Furthermore, the vector system is preferably an *Agrobacterium tumefaciens* Ti-plasmid or an *Agrobacterium rhizogenes* Ri-plasmid or a derivative thereof. As these plasmids are well-known and widely employed in the construction of transgenic plants, many vector systems exist which are based on these plasmids or derivatives thereof.

In the construction of a transgenic plant the nucleotide sequence or construct of the present invention may be first constructed in a microorganism in which the vector can replicate and which is easy to manipulate before insertion into the plant. An example of a useful microorganism is *E. coli*, but other microorganisms having the above properties may be used. When a vector of a vector system as defined above has been constructed in *E. coli*, it is transferred, if necessary, into a suitable Agrobactepium strain, e.g. *Agrobacterium tumefaciens*. The Ti-plasmid harbouring the nucleotide sequence or construct of the present invention is thus preferably transferred into a suitable Agrobacterium strain, e.g. *A. tumefaciens*, so as to obtain an Agrobacterium cell harbouring the promoter or nucleotide sequence or construct of the present invention, which DNA is subsequently transferred into the plant cell to be modified.

If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B.B., Alblasserdam, 1985, Chapter V; Fraley, et al., Crit. Rev. Plant Sci., 4:1–46; and An et al., EMBO J. (1985) 4:277–284.

Direct infection of plant tissues by Agrobacterium is a simple technique which has been widely employed and which is described in Butcher D. N. et al. (1980), Tissue Culture Methods for Plant Pathologists, eds.: D. S. Ingrams and J. P. Helgeson, 203–208. For further teachings on this topic see Potrykus (Annu Rev Plant Physiol Plant Mol Biol [1991] 42:205–225) and Christou (Agro-Food-Industry Hi-Tech March/April 1994 17–27). With this technique, infection of a plant may be performed in or on a certain part or tissue of the plant, i.e. on a part of a leaf, a root, a stem or another part of the plant.

Typically, with direct infection of plant tissues by Agrobacterium carrying the GOI (such as the nucleotide sequence according to the present invention) and, optionally, a promoter, a plant to be infected is wounded, e.g. by cutting the plant with a razor blade or puncturing the plant with a needle or rubbing the plant with an abrasive. The wound is then inoculated with the Agrobacterium. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc.

Regeneration of the transformed cells into genetically modified plants may be accomplished using known methods for the regeneration of plants from cell or tissue cultures, for example by selecting transformed shoots using an antibiotic and by subculturing the shoots on a medium containing the appropriate nutrients, plant hormones, etc.

Further teachings on plant transformation may be found in EP-A-0449375.

As reported in CA-A-2006454, a large amount of cloning vectors are available which contain a replication system in *E. coli* and a marker which allows a selection of the transformed cells. The vectors contain for example pBR 322, pUC series, M13 mp series, pACYC 184 etc. In this way, the nucleotide or construct of the present invention can be introduced into a suitable restriction position in the vector. The contained plasmid is then used for the transformation in *E. coli*. The *E. coli* cells are cultivated in a suitable nutrient medium and then harvested and lysed. The plasmid is then recovered. As a method of analysis there is generally used sequence analysis, restriction analysis, electrophoresis and further biochemical-molecular biological methods. After each manipulation, the used DNA sequence can be restricted and connected with the next DNA sequence. Each sequence can be cloned in the same or different plasmid.

After the introduction of the nucleotide sequence or construct according to the present invention in the plants the presence and/or insertion of further DNA sequences may be necessary—such as to create combination systems as outlined above (e.g. an organism comprising a combination of constructs).

The above commentary for the transformation of prokaryotic organisms and plants with the nucleotide sequence of the present invention is equally applicable for the transformation of those organisms with the promoter of the present invention.

In summation, the present invention relates to affecting enzyme activity by expressing sense intron sequences.

Also, the present invention relates to a promoter useful for the expression of those sense intron sequences.

The following samples have been deposited in accordance with the Budapest Treaty at the recognised depositary The National Collections of Industrial and Marine Bacteria Limited (NCIMB) at 23 St Machar Drive, Aberdeen, Scotland, AB2 1RY, United Kingdom, on Jul. 13, 1995:

NCIMB 40754 (which refers to pBEA 11 as described herein);
NCIMB 40751 (which refers to λ-SBE 3.2 as described herein), and
NCIMB 40752 (which refers to λ-SBE 3.4 as described herein).

A highly preferred embodiment of the present invention therefore relates to a method of affecting enzymatic activity in a plant (or a cell, a tissue or an organ thereof) comprising expressing in the plant (or a cell, a tissue or an organ thereof) a nucleotide sequence wherein the nucleotide sequence codes, partially or completely, for an intron in a sense orientation; wherein the nucleotide sequence does not contain a sequence that is sense to an exon sequence normally associated with the intron; wherein starch branching enzyme activity is affected and/or the levels of amylopectin are affected and/or the composition of starch is changed; and wherein the intron nucleotide sequence is obtainable from NCIMB 40751, NCIMB 40752, or NCIMB 40754 or a variant, derivative or homologue thereof.

A more highly preferred aspect of the present invention therefore relates to a method of affecting enzymatic activity in a plant (or a cell, a tissue or an organ thereof) comprising expressing in the plant (or a cell, a tissue or an organ thereof) a nucleotide sequence wherein the nucleotide sequence codes, partially or completely, for an intron in a sense orientation; wherein the nucleotide sequence does not contain a sequence that is sense to an exon sequence normally associated with the intron; wherein starch branching enzyme activity is affected and/or the levels of amylopectin are affected and/or the composition of starch is changed; wherein the nucleotide sequence comprises the sequence shown as any one of SEQ.I.D. No. 1 to SEQ.I.D. No. 13 or a variant, derivative or homologue thereof, including combinations thereof; and wherein the intron nucleotide sequence is obtainable from NCIMB 40751, NCIMB 40752, or NCIMB 40754, or a variant, derivative or homologue thereof.

Figure 3:
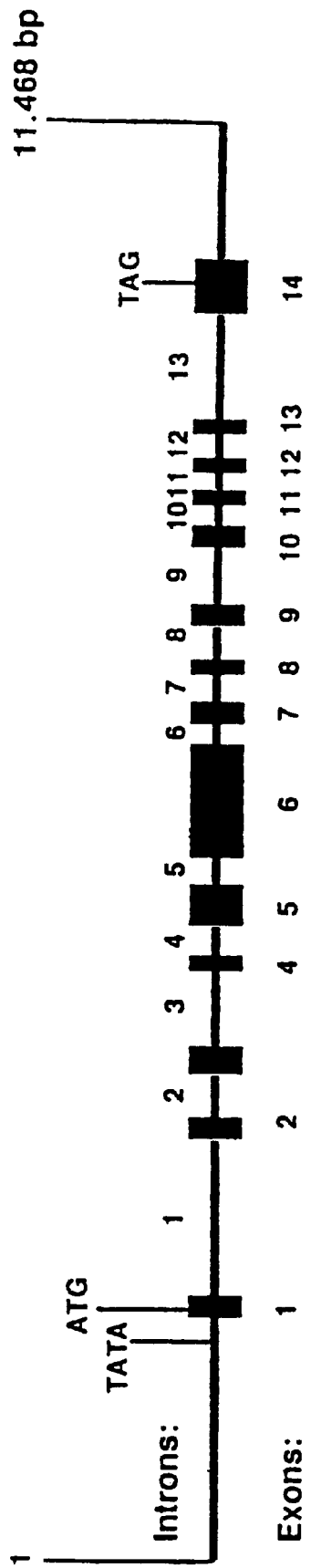
Figure 4:
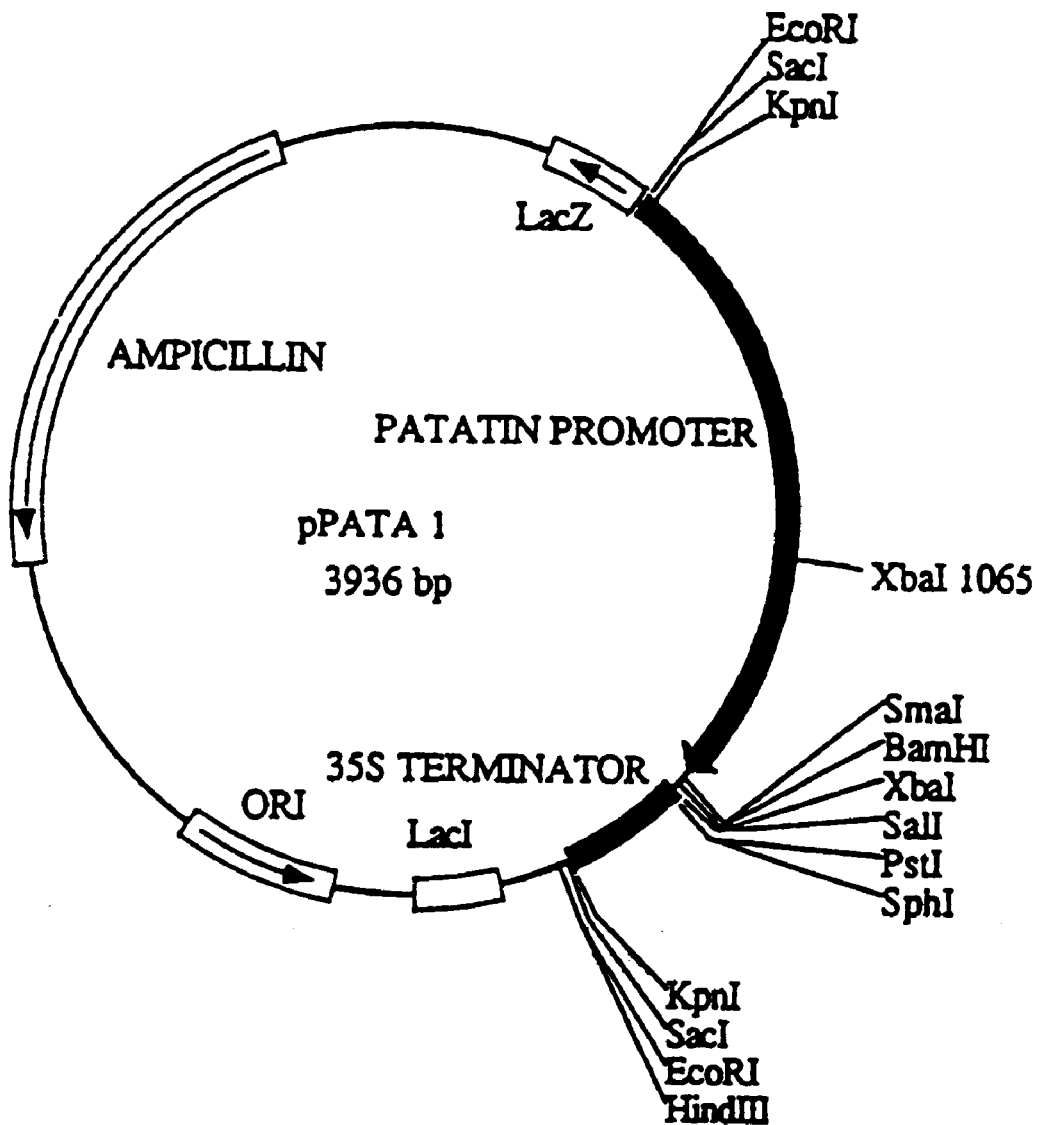
Figure 5:
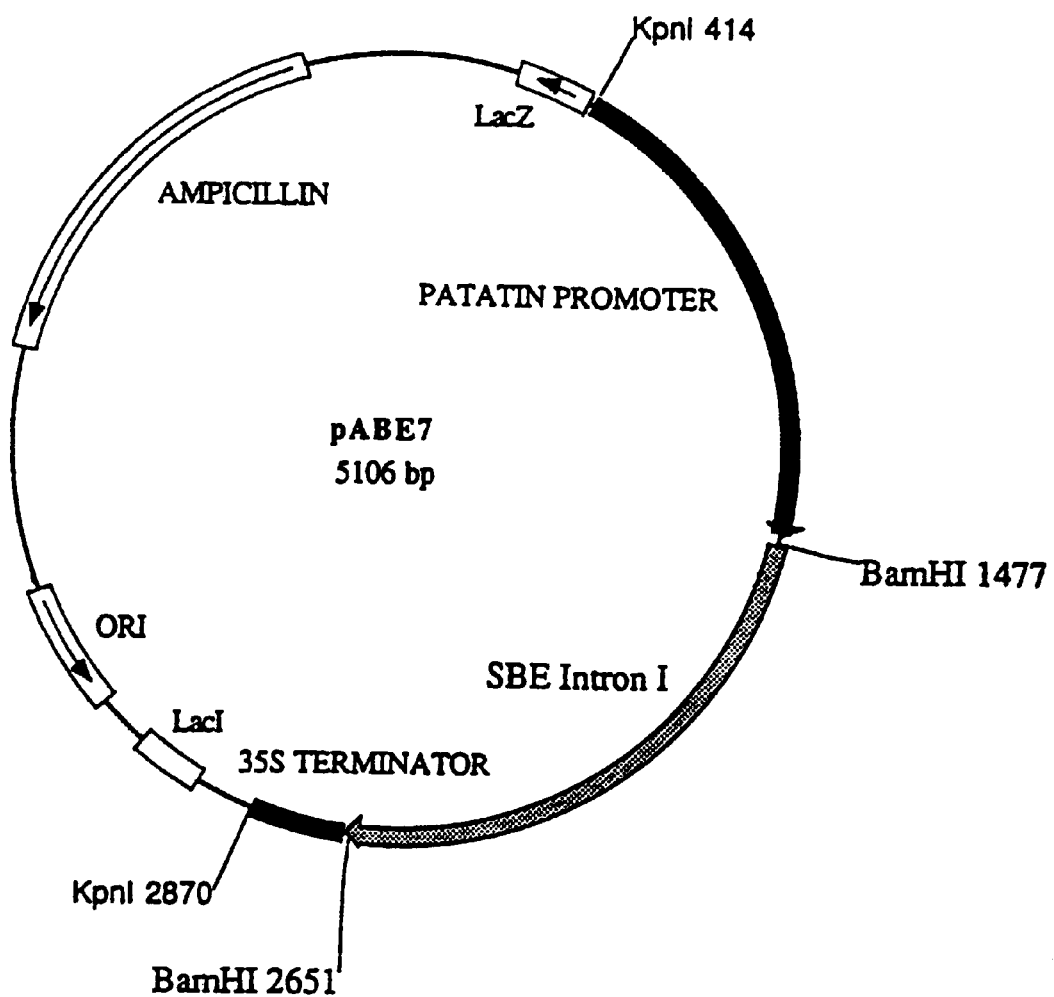
Figure 6:
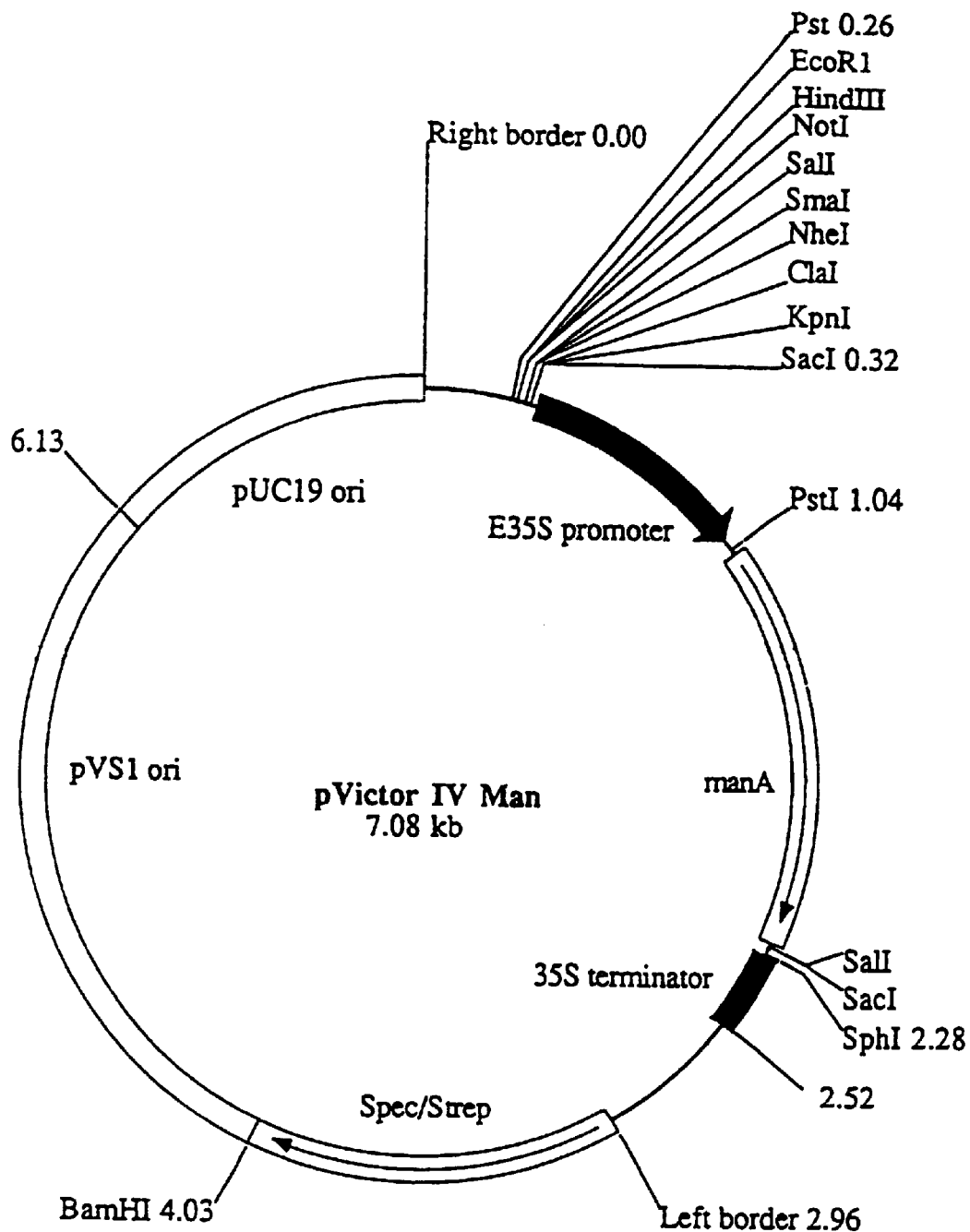
Figure 7:
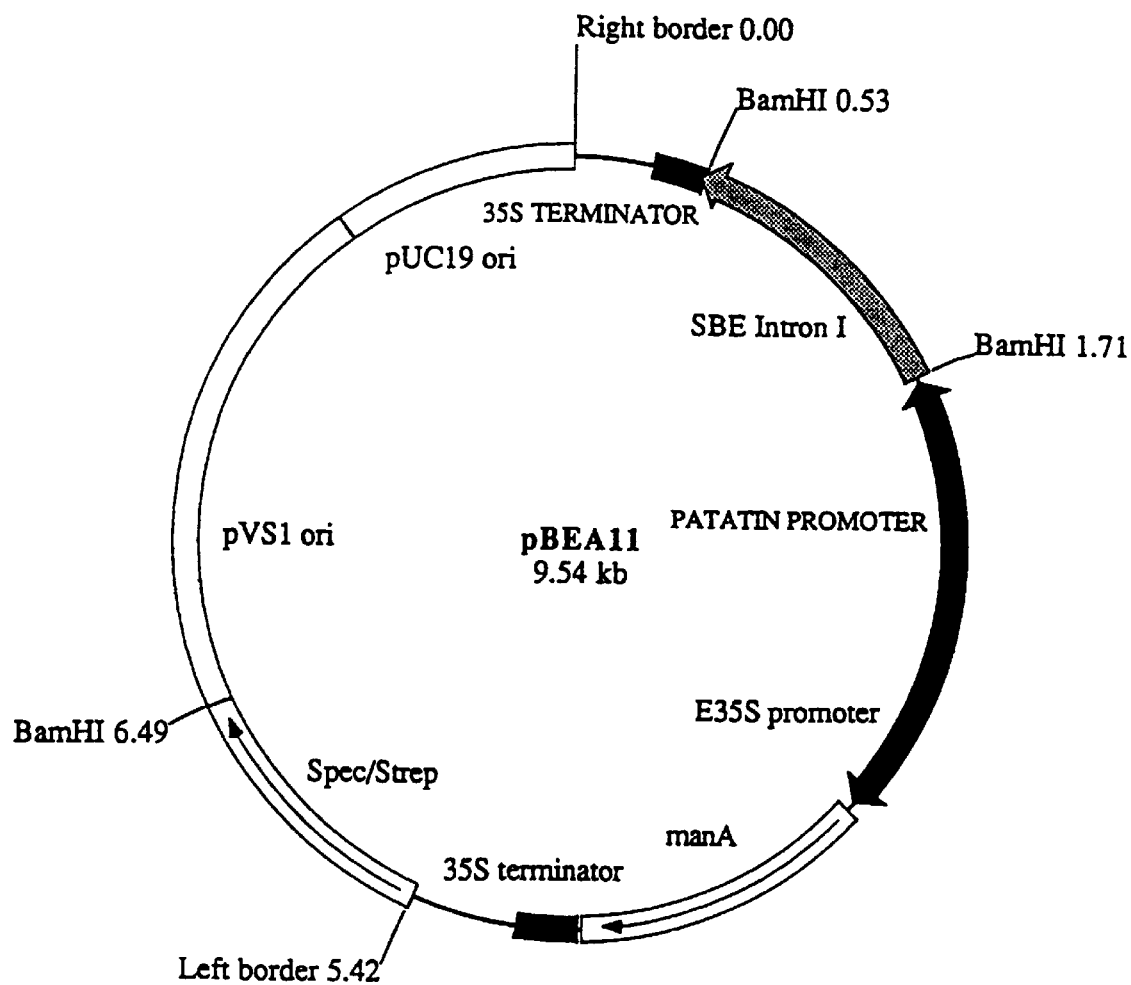
Figure 9:
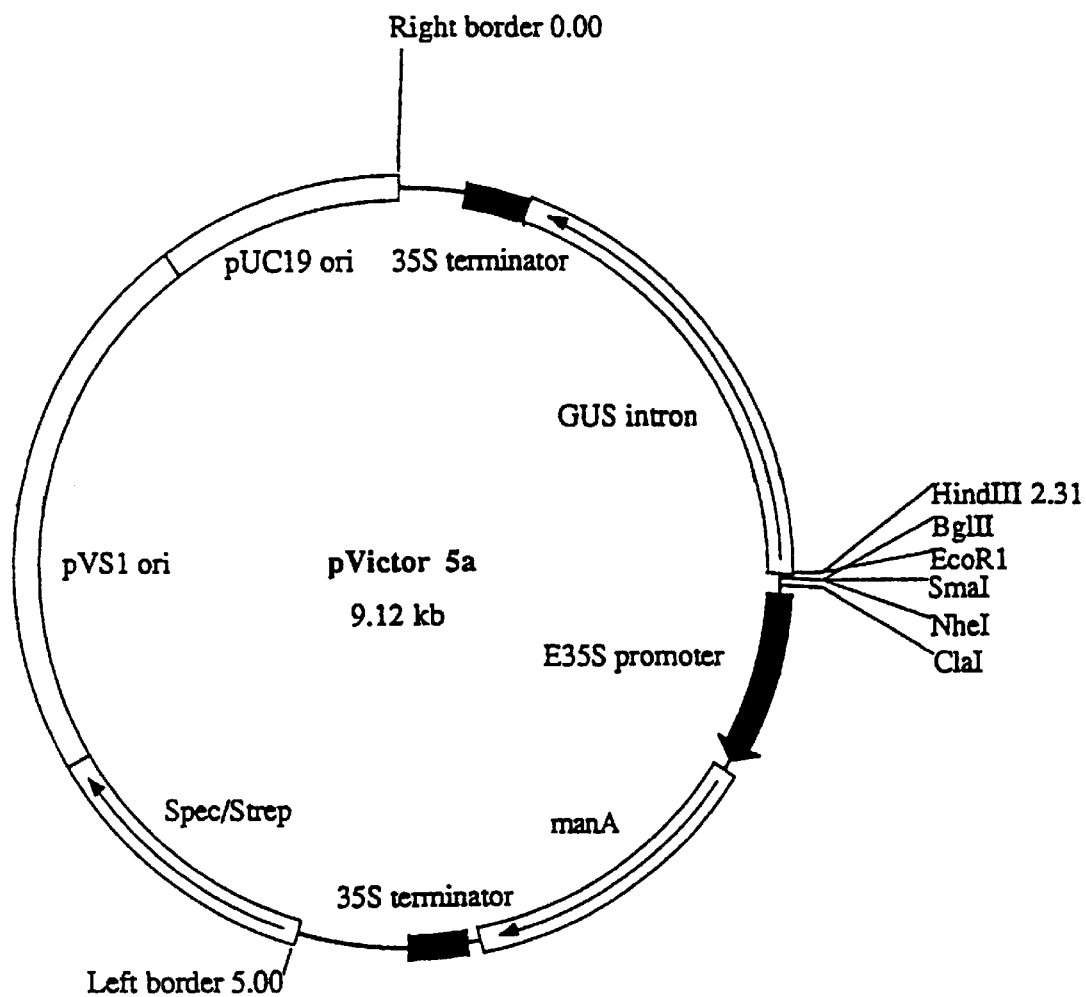

The present invention will now be described only by way of example, in which reference is made to the following attached Figures:

FIG. 1, which is a schematic representation of the biosynthesis of amylose and amylopectin;

FIG. 2, which is a diagrammatic representation of the α-1-4-links and the α-1-6 links of amylopectin;

FIG. 3, which is a diagrammatic representation of the exon-intron structure of a genomic SBE clone;

FIG. 4, which is a plasmid map of pPATA1, which is 3936 bp in size;

FIG. 5, which is a plasmid map of pABE7, which is 5106 bp in size;

FIG. 6, which is a plasmid map of pVictorIV Man, which is 7080 bp in size;

FIG. 7, which is a plasmid map of pBEA11, which is 9.54 kb in size;

FIG. 8, which shows the full genomic nucleotide sequence for SBE including the promoter, exons and introns;

FIG. 9, which is a plasmid map of pVictor5a, which is 9.12 kb in size; and

Figure 10:
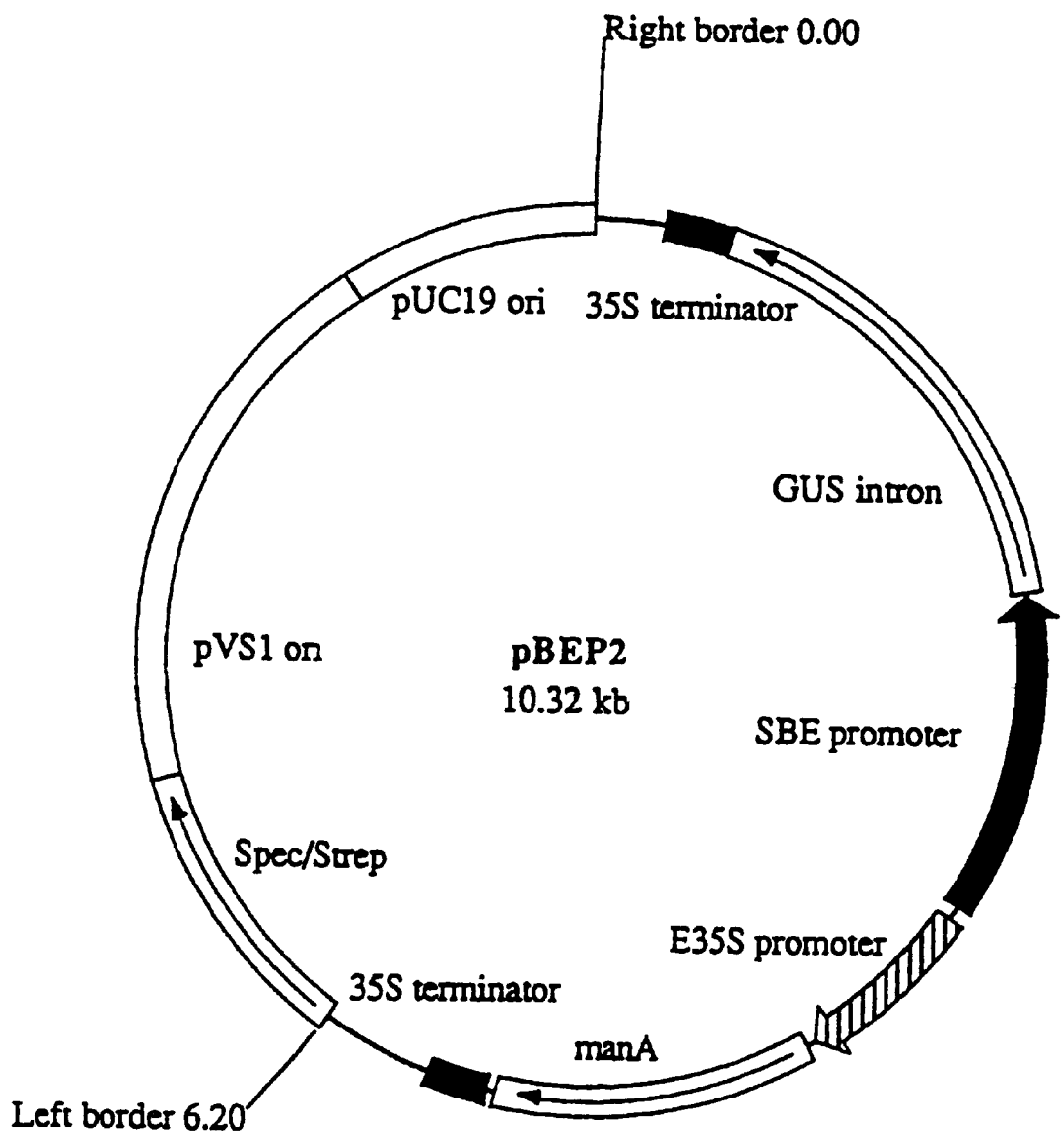

FIG. 10, which is a plasmid map of pBEP2, which is 10.32 kb in size.

FIGS. 1 and 2 were referred to above in the introductory description concerning starch in general. As mentioned, FIG. 3 is a diagrammatic representation of the exon-intron structure of a genomic SBE clone, the sequence of which is shown in FIG. 8. This clone, which has about 11.5 k base pairs, comprises 14 exons and 13 introns. The introns are numbered in increasing order from the 5' end to the 3' end and correspond to SEQ.I.D.No.s 1–13, respectively. Their respective antisense intron sequences are shown as SEQ.I.D-.No.s 15–27.

In more detail, FIGS. 3 and 8 present information on the 11468 base pairs of a potato SBE gene. The 5' region from nucleotides 1 to 2082 contain the promoter region of the SBE gene. A TATA box candidate at nucleotide 2048 to 2051 is boxed. The homology between a potato SBE cDNA clone (Poulsen & Kreiberg (1993) Plant Physiol 102: 1053–1054) and the exon DNAs begin at 2083 bp and end at 9666 bp. The homology between the cDNA and the exon DNA is indicated by nucleotides in upper case letters, while the translated amino acid sequences are shown in the single letter code below the exon DNA. Intron sequences are indicated by lower case letters.

FIG. 7 is a plasmid map of pBEA7, which is 9.54 k base pairs in size. Plasmid pBEA 11 comprises the first intron sequence of the potato SBE gene. This first intron sequence, which has 1177 base pairs, is shown in FIG. 3 and lies between the first exon and the second exon.

These experiments and aspects of the present invention are now discussed in more detail.

Experimental Protocol

Isolation, Subcloning in Plasmids, and Sequencing of Genomic SBE Clones

Various clones containing the potato SBE gene were isolated from a Desiree potato genomic library (Clontech Laboratories Inc., Palo Alto Calif., USA) using radioactively labelled potato SBE cDNA (Poulsen & Kreiberg (1993) Plant Physiol. 102:1053–1054) as probe. The fragments of the isolated λ-phages containing SBE DNA (XSBE 3.2—NCIMB 40751—and λSBE-3.4—NCIMB 40752) were identified by Southern analysis and then subcloned into pBluescript II vectors (Clontech Laboratories Inc., Palo Alto Calif., USA). λSBE 3.2 contains a 15 kb potato DNA insert and λSBE-3.4 contains a 13 kb potato DNA insert. The resultant plasmids were called pGB3, pGB11, pGB15, pGB16 and pGB25 (see discussion below). The respective inserts were then sequenced using the Pharmacia Autoread Sequencing Kit (Pharmacia, Uppsala) and a A.L.F. DNA sequencer (Pharmacia, Uppsala).

In total, a stretch of 11.5 kb of the SBE gene was sequenced. The sequence was deduced from the above-mentioned plasmids, wherein: pGB25 contains the sequences from 1 bp to 836 bp, pGB15 contains the sequences from 735 bp to 2580 bp, pGB16 contains the sequences from 2580 bp to 5093 bp, pGBI contains the sequences from 3348 bp to 7975 bp, and pGB3 contains the sequences from 7533 bp to 11468 bp.

In more detail, pGB3 was constructed by insertion of a 4 kb EcoRI fragment isolated from λSBE 3.2 into the EcoRI site of pBluescript II SK (+). pGB11 was constructed by insertion of a 4.7 kb XhoI fragment isolated from λSBE 3.4 into the XhoI site of pBluescript II SK (+). pGB15 was constructed by insertion of a 1.7 kb SpeI fragment isolated from λSBE 3.4 into the SpeI site of pBluescript II SK (+). pGB16 was constructed by insertion of a 2.5 kb SpeI fragment isolated from λSBE 3.4 into the SpeI site of pBluescript II SK (+). For the construction of pGB25 a PCR fragment was produced with the primers

5' GGA ATT CCA GTC GCA GTC TAC ATT AC 3' SEQ ID NO: 30 and

5' CGG GAT CCA GAG GCA TTA AGA TTT CTG G 3' SEQ ID NO: 31 and XSBE 3.4 as a template.

The PCR fragment was digested with BamHI and EcoRI, and inserted in pBluescript II SK (+) digested with the same restriction enzymes.

Construction of Plasmid pBEA11

The SBE intron 1 was amplified by PCR using the oligonucleotides

5' CGG GAT CCA AAG AAA TTC TCG AGG TTA CAT GG 3' SEQ ID NO: 32 and

5' CGG GAT CCG GGG TAA TTT TTA CTA ATT TCA TG 3' SEQ ID NO: 33 and the XSBE 3.4 phage containing the SBE gene as template.

The PCR product was digested with BamBI and inserted in a sense orientation in the BamHI site of plasmid pPATAI (described in WO 94/24292) between the patatin promoter and the 35S terminator. This construction, pABE7, was digested with KpnI, and the 2.4 kb "patatin promoter-SBE intron 1-c35S terminator" Kpnw fragment was isolated and inserted in the KpnI site of the plant transform ation vector pVictorIV Man yielding plasmid pBEA11.

Production of Transgenic Potato Plants

Axenic Stock Cultures

Shoot cultures of *Solanum tuberosum* 'Bintie' and 'Dianella' are maintained on a substrate (LS) of a formula according to Linsmaier, E. U. and Skoog, F. (1965), Physiol. Plant. 18: 100–127, in addition containing 2 μM silver thiosulphate at 25° C. and 16 h light/B h dark.

The cultures were subcultured after approximately 40 days. Leaves were then cut off the shoots and cut into nodal segments (approximately 0.8 cm) each containing one node.

Inoculation of Potato Tissues

Shoots from approximately 40 days old shoot cultures (height approximately 5–6 cms) were cut into internodal segments (approximately 0. 8 cm). The segments were placed into liquid LS-substrate containing the transformed *Agrobacterium tumefaciens* containing the binary vector of interest. The Agrobacterium were grown overnight in YMB-substrate (di-potassium hydrogen phosphate, trihydrate (0.66 g/l); magnesium sulphate, heptahydrate (0.20 g/l); sodium chloride (0.10 g/l); mannitol (10.0 g/l); and yeast extract (0.40 g/l)) containing appropriate antibiotics (corresponding to the resistance gene of the Agrobacterium strain) to an optical density at 660 nm (OD-660) of approximately 0.8, centrifuged and resuspended in the LS-substrate to an OD-660 of 0.5.

The segments were left in the suspension of Agrobacterium for 30 minutes and then the excess of bacteria were removed by blotting the segments on sterile filter paper.

Co-Cultivation

The shoot segments were co-cultured with bacteria for 48 hours directly on LS-substrate containing agar (8.0 g/l), 2,4-dichlorophenoxyacetic acid (2.0 mg/l) and trans-zeatin (0.5 mg/l). The substrate and also the explants were covered with sterile filter papers, and the petri dishes were placed at 25° C. and 16 h light/ 8 dark.

"Washing" Procedure

After the 48 h on the co-cultivation substrate the segments were transferred to containers containing liquid LS-substrate containing 800 mg/l carbenicillin. The containers were gently shaken and by this procedure the major part of the Agrobacterium was either washed off the segments and/or killed.

Selection

After the washing procedure the segments were transferred to plates containing the LS-substrate, agar (8 g/l), trans-zeatin (1–5 mg/1), gibberellic acid (0.1 mg/l), carbenicillin (800 mg/l), and kanamycin sulphate (50–100 mg/1) or phosphinotricin (1–5 mg/l) or mannose (5 g/l) depending on the vector construction used. The segments were subcultured to fresh substrate each 3–4 weeks. In 3 to 4 weeks, shoots develop from the segments and the formation of new shoots continued for 3–4 months.

Rooting of Regenerated Shoots

The regenerated shoots were transferred to rooting substrate composed of LS-substrate, agar (8 g/l) and carbenicillin (800 mg/l).

The transgenic genotype of the regenerated shoot were verified by testing the rooting ability on the above mentioned substrates containing kanamycin sulphate (200 mg/l), by performing NPTII assays (Radke, S. E. et al, Theor. Appl. Genet. (1988), 75: 685–694) or by performing PCR analysis according to Wang et al (1993, NAR 21 pp 4153–4154). Plants which were not positive in any of these assays were discarded or used as controls. Alternatively, the transgenic plants could be verified by performing a GUS assay on the co-introduced β-glucuronidase gene according to Hodal, L. et al. (Pl. Sci. (1992), 87: 115–122).

Transfer to Soil

The newly rooted plants (height approx. 2–3 cms) were transplanted from rooting substrate to soil and placed in a growth chamber (21° C., 16 hour light 200–400 uE/m$^2$/sec). When the plants were well established they were transferred to the greenhouse, where they were grown until tubers had developed and the upper part of the plants were senescing.

Harvesting

The potatoes were harvested after about 3 months and then analysed.

Branching Enzyme Analysis

The SBE expression in the transgenic potato lines were measured using the SBE assays described by Blennow and Johansson (Phytochemistry (1991) 30:437–444) and by standard Western procedures using antibodies directed against potato SBE.

Starch Analysis

Starch was isolated from potato tubers and analysed for the amylose:amylopectin ratio (Hovenkamp-Hermelink et al. (1988) Potato Research 31:241–246). In addition, the chain length distribution of amylopectin was determined by analysis of isoamylase digested starch on a Dionex HPAEC. The number of reducing ends in isoamylase digested starch was determined by the method described by N. Nelson (1944) J. Biol.Chem. 153:375–380.

The results revealed that there was a reduction in the level of synthesis of SBE and/or the level of activity of SBE and/or the composition of starch SBE in the transgenic plants.

Construction of SBE Promoter Construct

An SBE promoter fragment was amplified from λ-SBE 3.4 using primers:
5' CCA TCG ATA CTT TAA GTG ATT TGA TGG C 3' SEQ ID NO: 34
and
5' CGG GAT CCT GTT CTG ATT CTT GAT TTC C 3' SEQ ID NO: 35.

The PCR product was digested with ClaI and BamHI. The resultant 1.2 kb fragment was then inserted in pVictor5a (see FIG. 9) linearised with ClaI and BgII yielding pBEP2 (see FIG. 10).

Starch Branching Enzyme Measurements of Potato Tubers

Potatoes from potato plants transformed with pBEA11 were cut in small pieces and homogenised in extraction buffer (50 mM Tris-HCl pH 7.5, Sodium-dithionit (0.1 g/l), and 2 mM DTT) using a Ultra-Turax homogenizer; 1 g of Dowex xl. was added pr. 10 g of tuber. The crude homogenate was filtered through a miracloth filter and centrifuged at 4° C. for 10 minutes at 24.700 g. The supernatant was used for starch branching enzyme assays.

The starch branching enzyme assays were carried out at 25° C. in a volume of 400 μL composed of 0.1 M Na citrate buffer pH 7.0, 0.75 mg/ml amylose, 5 mg/ml bovine serum albumin and the potato extract. At 0, 15 30 and 60 minutes aliqouts of 50 μl were removed from the reaction into 20 Al 3 N HCl. 1 ml of iodine solution was added and the decrease in absorbance at 620 nm was measured with an ELISA spectrophotometer.

The starch branching enzyme (SBE) levels in tuber extracts were measured from 24 transgenic Dianella potato plants transformed with plasmid pBEA11.

The results showed that the BEA11 transgenic lines produced tubers which have SBE levels that are only 10% to 15% of the SBE levels found in non transformed Dianella plants.

Summation

The above-mentioned examples relate to the isolation and sequencing of a gene for potato SBE. The examples further demonstrate that it is possible to prepare SBE intron constructs. These SBE intron constructs can be introduced into plants, such as potato plants. After introduction, a reduction in the level of synthesis of SBE and/or the level of activity of SBE and/or the composition of starch in plants can be achieved.

Without wishing to be bound by theory it is believed that the expressed sense intron nucleotide sequence according to the present invention affects enzymatic activity via co-suppression and/or trans-activation. Reviews of these mechanisms has been published by Finnegan and McElroy (1994 Biotechnology 12 pp 883–887) and Matzke and Matzke (1995 TIG 11 No. 1 pp 1–3). By these mechanisms, it is believed that the sense introns of the present invention reduce the level of plant enzyme activity (in particular SBE activity), which in turn for SBE activity is believed to influence the amylose:amylopectin ratio and thus the branching pattern of amylopectin.

Thus, the present invention provides a method wherein it is possible to manipulate the starch composition in plants, or tissues or cells thereof, such as potato tubers, by reducing the level of SBE activity by using sense intron sequences.

In summation the present invention therefore relates to the surprising use of sense intron sequences in a method to affect enzymatic activity in plants.

Other modifications of the present invention will be apparent to those skilled in the art without departing from the scope of the present invention. For example, it may be possible to use antisense promoter sequences to affect enzymatic activity, such as antisense SBE promoter—such as a nucleotide sequence comprising the nucleotide sequence shown as SEQ. I.D. No. 28 or a variant, derivative or homologue thereof.

The following pages present a number of sequence listings which have been consecutively numbered from SEQ.I.D. No. 1–SEQ.I.D. No. 29. In brief, SEQ.I.D. No. 1–SEQ.I.D. No. 13 represent sense intron sequences (genomic DNA); SEQ.I.D. No. 14 represents the SBE promoter sequence (genomic sequence); SEQ.I.D. No. 15–SEQ.I.D. No. 27 represent antisense intron sequences; and SEQ. I.D. No. 28 represents the sequence complementary to the SBE promoter sequence—i.e. the SBE promoter sequence in antisense orientation. The full genomic nucleotide sequence for SBE including the promoter, exons and introns is shown as SEQ. I.D. No. 29 (see FIGS. 3 and 8 which highlight particular gene features).

What is claimed is:

1. A method of selectively affecting starch branching enzymatic (SBE) activity in a starch producing organism comprising expressing in the starch producing organism a nucleotide sequence wherein the nucleotide sequence codes for an intron, or an intron fragment, of an SBE gene in a sense orientation; and wherein the nucleotide sequence does not contain a sequence that is sense to an exon sequence normally associated with the intron.

2. The method according to claim 1, wherein the starch producing organism comprises a biological sample derived therefrom, selected from the group consisting of a cell, cell line, tissue and organ.

3. The method according to claim 1, wherein the levels of amylopectin are changed.

4. The method according to claim 1, wherein the composition of starch is changed in the starch producing organism.

5. The method according to claim 1, wherein the starch producing organism is a plant.

6. The method according to claim 1, wherein the nucleotide sequence does not contain a sequence that is sense to an exon sequence.

7. The method according to claim 1, wherein the enzymatic activity is reduced.

8. The method according to claim 1, wherein the nucleotide sequence codes for at least a portion of one intron fragment in a sense orientation.

9. The method according to claim 1, wherein the nucleotide sequence codes for at least one entire one intron in a sense orientation.

10. A method of affecting starch branching enzymatic (SBE) activity in a starch producing organism comprising expressing in the starch producing organism a nucleotide sequence wherein the nucleotide sequence codes for an intron, or an intron fragment, of an SBE gene in a sense orientation; wherein the nucleotide sequence does not contain a sequence that is sense to an exon sequence normally associated with the intron; and wherein the nucleotide sequence comprises a sequence as shown as any one of SEQ.ID. No. 1 to SEQ.ID. No. 13 or a variant, derivative or homologue thereof, including combinations thereof.

11. The method of claim 10 wherein the nucleotide sequence comprises a sequence as shown as any one of SEQ.ID. No. 1 to SEQ.ID. No. 13 or combinations thereof.

12. The method of claim 10 wherein the nucleotide sequence comprises a sequence as shown as any one of SEQ.ID. No. 1 to SEQ.ID. No. 13.

13. The method of claim 10 wherein the nucleotide sequence comprises a sequence as shown as SEQ.ID. No. 1.

14. The method of claim 10 wherein the nucleotide sequence comprises a sequence as shown as SEQ.ID. No. 2.

15. The method of claim 10 wherein the nucleotide sequence comprises a sequence as shown as SEQ.ID. No. 3.

16. The method of claim 10 wherein the nucleotide sequence comprises a sequence as shown as SEQ.ID. No. 4.

17. The method of claim 10 wherein the nucleotide sequence comprises a sequence as shown as SEQ.ID. No. 5.

18. The method of claim 10 wherein the nucleotide sequence comprises a sequence as shown as SEQ.ID. No. 6.

19. The method of claim 10 wherein the nucleotide sequence comprises a sequence as shown as SEQ.ID. No. 7.

20. The method of claim 10 wherein the nucleotide sequence comprises a sequence as shown as SEQ.ID. No. 8.

21. The method of claim 10 wherein the nucleotide sequence comprises a sequence as shown as SEQ.ID. No. 9.

22. The method of claim 10 wherein the nucleotide sequence comprises a sequence as shown as SEQ.ID. No. 10.

23. The method of claim 10 wherein the nucleotide sequence comprises a sequence as shown as SEQ.ID. No. 11.

24. The method of claim 10 wherein the nucleotide sequence comprises a sequence as shown as SEQ.ID. No. 12.

25. The method of claim 10 wherein the nucleotide sequence comprises a sequence as shown as SEQ.ID. No. 13.

26. The method according to claim 10, wherein the starch producing organism comprises a biological sample derived therefrom, selected from the group consisting of a cell, cell line, tissue or organ.

27. The method according to claim 10, wherein the levels of amylopectin are changed.

28. The method according to claim 10, wherein the composition of starch is changed in the starch producing organism.

29. An isolated nucleic acid molecule encoding an intron or an intron fragment, of an starch branching enzymatic (SBE) gene in a sense orientation comprising a sequence as shown as any one of SEQ.ID. No. 1 to SEQ.ID. No. 13 or a variant, derivative or homologue thereof.

30. The isolated nucleic acid molecule of claim 28 wherein comprising a sequence as shown as any one of SEQ.ID. No. 1 to SEQ.ID. No. 13.

31. The isolated nucleic acid molecule of claim 28 wherein comprising a sequence as shown as SEQ.ID. No. 1.

32. The isolated nucleic acid molecule of claim 28 wherein comprising a sequence as shown as SEQ.ID. No. 2.

33. The isolated nucleic acid molecule of claim 28 wherein comprising a sequence as shown as SEQ.ID. No. 3.

34. The isolated nucleic acid molecule of claim 28 wherein comprising a sequence as shown as SEQ.ID. No. 4.

35. The isolated nucleic acid molecule of claim 28 wherein comprising a sequence as shown as SEQ.ID. No. 5.

36. The isolated nucleic acid molecule of claim 28 wherein comprising a sequence as shown as SEQ.I.D. No. 6.

37. The isolated nucleic acid molecule of claim 28 wherein comprising a sequence as shown as SEQ.ID. No.7.

38. The isolated nucleic acid molecule of claim 28 wherein comprising a sequence as shown as SEQ.ID. No. 8.

39. The isolated nucleic acid molecule of claim 28 wherein comprising a sequence as shown as SEQ.ID. No. 9.

40. The isolated nucleic acid molecule of claim 28 wherein comprising a sequence as shown as SEQ.ID. No.10.

41. The isolated nucleic acid molecule of claim 28 wherein comprising a sequence as shown as SEQ.ID. No.11.

42. The isolated nucleic acid molecule of claim 28 wherein comprising a sequence as shown as SEQ.ID. No. 12.

43. The isolated nucleic acid molecule of claim 28 wherein comprising a sequence as shown as SEQ.ID. No.13.

44. A method of affecting starch branching enzymatic (SBE) activity in a starch producing organism comprising expressing in the starch producing organism a nucleotide sequence wherein the nucleotide sequence codes, for an intron, or an intron fragment, of an SBE gene in a sense orientation; wherein the nucleotide sequence does not contain a sequence that is sense to an exon sequence normally associated with the intron; and wherein the nucleotide sequence is expressed by a promoter having a sequence shown as SEQ.ID. No.14 or a variant, derivative or homologue thereof.

45. The method of claim 44 wherein the promoter comprises a sequence as shown as SEQ.ID.No. 14.

46. The method according to claim 44, wherein the starch producing organism comprises a biological sample derived therefrom, selected from the group consisting of a cell, cell line, tissue or organ.

47. A promoter having a sequence shown as SEQ.ID. No. 14, or a variant, derivative or homologue thereof.

48. The promoter of claim 47 having a sequence as shown as SEQ.ID.No. 14.

49. An isolated nucleic acid molecule having a sequence shown as SEQ.ID. No. 14, or a variant, derivative or homologue thereof.

50. The isolated nucleic acid molecule of claim 47 having a sequence as shown as SEQ.ID.No. 14.

51. The promoter according to claim 45, in combination with a gene of interest ("GOI").

52. A construct comprising the isolated nucleic acid molecule according to claim 50.

53. A construct comprising the promoter according to claim 45.

54. The construct according to claim 53, further comprising a gene of interest ("GOI").

55. A vector comprising the isolated nucleic acid molecule according to claim 50.

56. A vector comprising the promoter according to claim 45.

57. The vector according to claim 55, further comprising a gene of interest ("GOI").

58. A biological sample, selected from the group consisting of a cell, cell line, tissue or organ, containing the isolated nucleic acid molecule according to claim 50.

59. A biological sample, selected from the group consisting of a cell, cell line, tissue or organ, containing the promoter according to claim 45.

60. The biological sample according to claim 59, further comprising a gene of interest ("GOI").

61. A transgenic starch producing organism comprising or expressing the isolated nucleic acid molecule according to claim 28.

62. A transgenic starch producing organism containing the promoter according to claim 47.

63. The transgenic starch producing organism according to claim 62, further comprising a gene of interest ("GOI").

64. The transgenic starch producing organism according to any one of claims 61, 62, or 63, wherein the organism is a plant.

65. A starch obtained from the method of any one of claims 1, 2, 3, 4, 5, 6, 7 or 8.

66. pBEA11 (NCIMB 40754).

67. An isolated nucleic acid molecule comprising an intron nucleotide sequence that is obtainable from X-SBE 3.2 (NCIMB 40751) or a variant, derivative or homologue thereof.

68. The isolated nucleic acid molecule of claim 48 comprising an intron nucleotide sequence obtainable from X-SBE 3.2 (NCIMB 40751).

69. An isolated nucleic acid molecule comprising an intron nucleotide sequence that is obtainable from A-SBE 3.4 (NCIMB 40752) or a variant, derivative or homologue thereof.

70. The isolated nucleic acid molecule of claim 69 comprising an intron nucleotide sequence obtainable from X-SBE 3.4 (NCIMB 40752).

* * * * *

UNITED STATES PATENT AND TRADEMARK OFFICE
CERTIFICATE OF CORRECTION

PATENT NO. : 6,232,122 B1
DATED : May 15, 2001
INVENTOR(S) : Poulsen

Page 1 of 2

It is certified that error appears in the above-identified patent and that said Letters Patent is hereby corrected as shown below:

Column 16,
After line 50, insert:
-- NCIMB 40751, NCIMB 40752 and NCIMB 40754 were deposited with The National Collections of Industrial and Marine Bacteria Limited (NCIMB), 23 St. Machar Drive, Aberdeen, Scotland, AB2 1RY, United Kingdom, under the terms of the Budapest Treaty, on 13 July 1995.

Column 49, claim 30,
Line 10, delete "wherein";

Column 49, claim 31,
Line 13, delete "wherein";

Column 49, claim 32,
Line 15, delete "wherein";

Column 49, claim 33,
Line 17, delete "wherein";

Column 49, claim 34,
Line 19, delete "wherein";

Column 49, claim 35,
Line 21, delete "wherein";

Column 49, claim 36,
Line 23, delete "wherein";

Column 49, claim 37,
Line 25, delete "wherein";

Column 49, claim 38,
Line 27, delete "wherein";

Column 49, claim 39,
Line 29, delete "wherein";

Column 49, claim 40,
Line 31, delete "wherein";

UNITED STATES PATENT AND TRADEMARK OFFICE
CERTIFICATE OF CORRECTION

PATENT NO. : 6,232,122 B1
DATED : May 15, 2001
INVENTOR(S) : Poulsen

It is certified that error appears in the above-identified patent and that said Letters Patent is hereby corrected as shown below:

Column 49, claim 41,
Line 33, delete "wherein";

Column 49, claim 42,
Line 35, delete "wherein";

Column 49, claim 43,
Line 38, delete "wherein".

Signed and Sealed this

Thirteenth Day of November, 2001

Attest:

*Nicholas P. Godici*

NICHOLAS P. GODICI
*Attesting Officer*   *Acting Director of the United States Patent and Trademark Office*

SEQUENCE LISTING

```
<160> NUMBER OF SEQ ID NOS: 35

<210> SEQ ID NO: 1
<211> LENGTH: 1167
<212> TYPE: DNA
<213> ORGANISM: Solanum tuberosum
<220> FEATURE:
<221> NAME/KEY: variation
<222> LOCATION: (1)..(1167)
<223> OTHER INFORMATION: B stands for G or C or T/U
<220> FEATURE:
<221> NAME/KEY: variation
```

<222> LOCATION: (1)..(1167)
<223> OTHER INFORMATION: R stands for G or A

<400> SEQUENCE: 1

```
gtaatttttta ctaatttcat gttaatttca attattttta gcctttgcat ttcattttcc      60
aatatatctg gatcatctcc ttagttttt atttttatttt ttataatatc aaatatggaa      120
gaaaaatgac acttgtagag ccatatgtaa gtatcatgtg acaaatttgc aaggtggttg      180
agtgtataaa attcaaaaat tgagagatgg aggggggtg ggggbaraga caatatttag       240
aaagagtgtt ctaggaggtt atggaggaca cggatgaggg gtagaaggtt agttaggtat      300
ttgagtgttg tctggcttat cctttcatac tagtagtcgt ggaattattt gggtagtttc      360
ttgttttgtt atttgatctt tgttattcta ttttctgttt cttgtacttc gattattgta      420
ttatatatct tgtcgtagtt attgttcctc ggtaagaatg ctctagcatg cttcctttag      480
tgttttatca tgccttcttt atattcgcgt tgctttgaaa tgcttttact ttagccgagg      540
gtctattaga aacaatctct ctatctcgta aggtaggggt aaagtcctca ccacactcca      600
cttgtgggat tacattgtgt ttgttgttgt aaatcaatta tgtatacata ataagtggat      660
ttttttacaac acaaatacat ggtcaagggc aaagttctga acacataaag ggttcattat      720
atgtccaggg atatgataaa aattgtttct ttgtgaaagt tatataagat ttgttatggc      780
ttttgctgga aacataataa gttataatgc tgagatagct actgaagttt gttttttcta      840
gcctttttaaa tgtaccaata atagattccg tatcgaacga gtatgttttg attacctggt      900
catgatgttt ctattttta catttttttg gtgttgaact gcaattgaaa atgttgtatc       960
ctatgagacg gatagttgag aatgtgttct ttgtatggac cttgagaagc tcaaacgcta      1020
ctccaataat ttctatgaat tcaaattcag tttatggcta ccagtcagtc cagaaattag      1080
gatatgctgc atatacttgt tcaattatac tgtaaaattt cttaagttct caagatatcc      1140
atgtaacctc gagaatttct ttgacag                                           1167
```

<210> SEQ ID NO: 2
<211> LENGTH: 321
<212> TYPE: DNA
<213> ORGANISM: Solanum tuberosum
<220> FEATURE:
<221> NAME/KEY: variation
<222> LOCATION: (1)..(321)
<223> OTHER INFORMATION: B stands for G or C or T/U
<220> FEATURE:
<221> NAME/KEY: variation
<222> LOCATION: (1)..(321)
<223> OTHER INFORMATION: K stands for G or T/U

<400> SEQUENCE: 2

```
gtatgtttga taatttatat ggttgcatgg atagtatata aatagttgga aaacttctgg      60
actggtgctc atggcatatt tgatctgtgc accgtgtgga gatgtcaaac atgtgttact      120
tcgttccgcc aatttataat accttaactt gggaaagaca gctctttact cctgtgggca     180
tttgttattt gaattacaat ctttatgagc atggtgtttt cacattatca acttctttca     240
tgtggtatat aacagttttt agctccgtta ataccttctct tcttttgat ataaactaac      300
tgtggtgcat tgcttgcbkk k                                                321
```

<210> SEQ ID NO: 3
<211> LENGTH: 504
<212> TYPE: DNA
<213> ORGANISM: Solanum tuberosum -continued

```
<400> SEQUENCE: 3
gtaacagcca aaagttgtgc tttaggcagt ttgaccttat tttggaagat gaattgttta       60
tacctacttt gactttgcta gagaattttg cataccgggg agtaagtagt ggctccattt      120
aggtggcacc tggccatttt tttgatcttt taaaaagctg tttgattggg tcttcaaaaa      180
agtagacaag ttttttggag aagtgacaca cccccggagt gtcagtggca agcaaagat       240 tttcactaag gagattcaaa atataaaaaa agtatagaca taaagaagct gaggggattc      300
aacatgtact atacaagcat caaatatagt cttaaagcaa ttttgtagaa ataaagaaag      360
tcttccttct gttgcttcac aatttccttc tattatcatg agttactctt tctgttcgaa      420
atagcttcct taatattaaa ttcatgatac ttttgttgag atttagcagt ttttttcttgt     480 gtaaactgct ctcttttttt gcag                                             504

<210> SEQ ID NO: 4
<211> LENGTH: 146
<212> TYPE: DNA
<213> ORGANISM: Solanum tuberosum

<400> SEQUENCE: 4
gtaggtcctc gtctactaca aaatagtagt ttccatcatc ataacagatt ttcctattaa       60
agcatgatgt tgcagcatca ttggctttct tacatgttct aattgctatt aaggttatgc      120
ttctaattaa ctcatccaca atgcag                                           146

<210> SEQ ID NO: 5
<211> LENGTH: 218
<212> TYPE: DNA
<213> ORGANISM: Solanum tuberosum

<400> SEQUENCE: 5
gttttgttat tcataccttg aagctgaatt ttgaacacca tcatcacagg catttcgatt       60
catgttctta ctagtcttgt tatgtaagac attttgaaat gcaaaagtta aaataattgt      120
gtctttacta atttggactt gatcccatac tctttccctt aacaaaatga gtcaattcta      180
taagtgcttg agaacttact acttcagcaa ttaaacag                              218

<210> SEQ ID NO: 6
<211> LENGTH: 198
<212> TYPE: DNA
<213> ORGANISM: Solanum tuberosum

<400> SEQUENCE: 6
gtattttaaa tttatttcta caactaaata attctcagaa caattgttag atagaatcca       60
aatatatacg tcctgaaagt ataaagtac ttattttcgc catgggcctt cagaatattg       120
gtagccgctg aatatcatga taagttattt atccagtgac attttatgt tcactcctat       180 tatgtctgct ggatacag                                                    198

<210> SEQ ID NO: 7
<211> LENGTH: 208
<212> TYPE: DNA
<213> ORGANISM: Solanum tuberosum

<400> SEQUENCE: 7
gtttgtctgt ttctattgca ttttaaggtt catataggtt agccacggaa aatctcactc       60
tttgtgaggt aaccagggtt ctgatggatt attcaatttt ctcgtttatc atttgtttat      120
tcttttcatg cattgtgttt cttttttcaat atccctctta tttggaggta attttttctca    180
```

```
tctattcact tttagcttct aaccacag                                        208

<210> SEQ ID NO: 8
<211> LENGTH: 293
<212> TYPE: DNA
<213> ORGANISM: Solanum tuberosum

<400> SEQUENCE: 8
gtatgtctta catctttaga tattttgtga taattacaat tagtttggct tacttgaaca     60
agattcattc ctcaaaatga cctgaactgt tgaacatcaa aggggttgaa acatagagga   120
aaacaacatg atgaatgttt ccattgtcta gggatttcta ttatgttgct gagaacaaat   180
gtcatcttaa aaaaaacatt gtttactttt ttgtagtata gaagattact gtatagagtt   240
tgcaagtgtg tctgttttgg agtaattgtg aaatgtttga tgaacttgta cag           293

<210> SEQ ID NO: 9
<211> LENGTH: 376
<212> TYPE: DNA
<213> ORGANISM: Solanum tuberosum

<400> SEQUENCE: 9
gttcaagtat tttgaatcgc agcttgttaa ataatctagt aattttttaga ttgcttactt    60 ggaagtctac ttggttctgg ggatgatagc tcatttcatc ttgttctact tattttccaa   120
ccgaatttct gattttttgtt tcgagatcca agtattagat tcatttacac ttattaccgc   180
ctcatttcta ccactaaggc cttgatgagc agcttaagtt gattctttga agctatagtt   240
tcaggctacc aatccacagc ctgctatatt tgttggatac ttaccttttc tttacaatga   300
agtgatacta attgaaatgg tctaaatctg atatctatat ttctccgtct ttcctccccc   360
tcatgatgaa atgcag                                                    376

<210> SEQ ID NO: 10
<211> LENGTH: 172
<212> TYPE: DNA
<213> ORGANISM: Solanum tuberosum

<400> SEQUENCE: 10
gtaaaatcat ctaaagttga aagtgttggg tttatgaagt gctttaattc tatccaagga    60
caagtagaaa ccttttttacc ttccatttct tgatgatgga tttcatatta tttaatccaa   120
tagctggtca aattcggtaa tagctgtact gattagttac ttcactttgc ag            172

<210> SEQ ID NO: 11
<211> LENGTH: 145
<212> TYPE: DNA
<213> ORGANISM: Solanum tuberosum

<400> SEQUENCE: 11
gtatatatgt tttacttatc catgaaatta ttgctctgct tgttttttaat gtactgaaca    60 agttttatgg agaagtaact gaaacaaatc attttcacat tgtctaattt aactcttttt   120
tctgatcctc gcatgacgaa aacag                                          145

<210> SEQ ID NO: 12
<211> LENGTH: 242
<212> TYPE: DNA
<213> ORGANISM: Solanum tuberosum

<400> SEQUENCE: 12
```

-continued

```
gtaaggattt gcttgaataa cttttgataa taagataaca gatgtagggt acagttctct      60
caccaaaaag aactgtaatt gtctcatcca tctttagttg tataagatat ccgactgtct     120
gagttcggaa gtgtttgagc ctcctgccct ccccctgcgt tgtttagcta attcaaaaag     180
gagaaaactg tttattgatg atctttgtct tcatgctgac atacaatctg ttctcatgac     240
ag                                                                    242
```

<210> SEQ ID NO: 13
<211> LENGTH: 797
<212> TYPE: DNA
<213> ORGANISM: Solanum tuberosum

<400> SEQUENCE: 13

```
gtacagttct tgccgtgtga cctcccttt tattgtggtt ttgttcatag ttatttgaat       60
gcgatagaag ttaactattg attaccgcca caatcgccag ttaagtcctc tgaactacta    120
atttgaaagg taggaatagc cgtaataagg tctacttttg gcatcttact gttacaaaac    180
aaaaggatgc caaaaaaatt cttctctatc ctctttttcc ctaaaccagt gcatgtagct    240
tgcacctgca taaacttagg taaatgatca aaatgaagt tgatgggaac ttaaaaccgc     300
cctgaagtaa agctaggaat agtcatataa tgtccaccct tggtgtctgc gctaacatca    360
acaacaacat acctcgtgta gtcccacaaa gtggtttcag gggagggta gagtgtatgc     420 aaaacttact cctatctcag aggtagagag gatttttca atagacccct ggctcaagaa    480
aaaaagtcca aaagaagta acagaagtga agcaacatg tgtagctaaa gcacccaac      540 ttgtttggga ctgaagtagt tgttgttgtt gaaacagtgc atgtagatga acacatgtca    600
gaaaatggac aacacagtta ttttgtgcaa gtcaaaaaaa tgtactacta tttctttgtg    660
cagctttatg tatagaaaag ttaaataact aatgaatttt gctagcagaa aaatagcttg    720
gagagaaatt ttttatattg aactaagcta actatattca tctttctttt tgcttcttct    780
tctccttgtt tgtgaag                                                    797
```

<210> SEQ ID NO: 14
<211> LENGTH: 2169
<212> TYPE: DNA
<213> ORGANISM: Solanum tuberosum

<400> SEQUENCE: 14

```
atcatggcca attactggtt caaatgcatt acttcctttc agattctttc gagttctcat      60
gaccggtcct actacagacg atactaaccc gtggaactgt tgcatctgct tcttagaact    120
ctatggctat tttcgttagc ttggcgtcgg tttgaacata gttttttgttt tcaaactctt    180 catttacagt caaaatgttg tatggttttt gttttcctca atgatgttta cagtgttgtg    240
ttgtcatctg tacttttgcc tattacttgt tttgagttac atgttaaaaa agtgtttatt    300
ttgccatatt ttgttctctt attattatta tcatacatac attattacaa ggaaaagaca    360
agtcacagga tcttaacgtt tatgttcaat caacttttgg aggcattgac aggtaccaca    420
aattttgagt ttatgattaa gttcaatctt agaatatgaa tttaacatct attatagatg    480
cataaaaata gctaatgata gaacattgac atttggcaga gcttagggta tggtatatcc    540
aacgttaatt tagtaatttt tgttacgtac gtatatgaaa tattgaatta atcacatgaa    600
cggtggatat tatattatga gttggcatca gcaaaatcat tggtgtagtt gactgtagtt    660
gcagatttaa taataaaatg gtaattaacg gtcgatatta aaataactct catttcaagt    720
gggattagaa ctagttatta aaaaaatgta tactttaagt gatttgatgg catataattt    780
```

```
aaagtttttc atttcatgct aaaattgtta attattgtaa tgtagactgc gactggaatt      840
attatagtgt aaatttatgc attcagtgta aaattaaagt attgaacttg tctgttttag      900
aaaatacttt atactttaat ataggatttt gtcatgcgaa tttaaattaa tcgatattga      960
acacggaata ccaaaattaa aaaggataca catggccttc atatgaaccg tgaacctttg     1020
ataacgtgga agttcaaaga aggtaaagtt taagaataaa ctgacaaatt aatttctttt     1080
atttggccca ctactaaatt tgctttactt tctaacatgt caagttgtgc cctcttagtt     1140
gaatgatatt catttttcat cccataagtt caatttgatt gtcataccac ccatgatgtt     1200
ctgaaaaatg cttggccatt cacaaagttt atcttagttc ctatgaactt tataagaagc     1260
tttaatttga catgttattt atattagatg atataatcca tgacccaata gacaagtgta     1320
ttaatattgt aactttgtaa ttgagtgtgt ctacatctta ttcaatcatt taaggtcatt     1380
aaaataaatt attttttgac attctaaaac tttaagcaga ataaatagtt tatcaattat     1440
taaaaacaaa aaacgactta tttataaatc aacaaacaat tttagattgc tccaacatat     1500
ttttccaaat taaatgcaga aaatgcataa ttttatactt gatctttata gcttattttt     1560
tttagcctaa ccaacgaata tttgtaaact cacaacttga ttaaaaggga tttacaacaa     1620
gatatatata agtagtgaca aatcttgatt ttaaatattt taatttggag gtcaaaattt     1680
taccataatc atttgtattt ataattaaat tttaaatatc ttatttatac atatctagta     1740
aacttttaaa tatacgtata tacaaaatat aaaattattg gcgttcatat taggtcaata     1800
aatccttaac tatatctgcc ttaccactag gagaaagtaa aaaactcttt accaaaaata     1860
catgtattat gtatacaaaa agtcgattag attacctaaa tagaaattgt ataacgagta     1920
agtaagtaga aatataaaaa aactacaata ctaaaaaaaa tatgttttac ttcaatttcg     1980
aaactaatgg ggtctgagtg aaatattcag aaagggagg actaacaaaa gggtcataat     2040 gttttttttat aaaaagccac taaatgaggg aaatcaagaa tcagaacata caagaaggca     2100
gcagctgaag caaagtacca taatttaatc aatggaaatt aatttcaaag ttttatcaaa     2160
acccattcg                                                             2169

<210> SEQ ID NO: 15
<211> LENGTH: 1167
<212> TYPE: DNA
<213> ORGANISM: Solanum tuberosum
<220> FEATURE:
<221> NAME/KEY: variation
<222> LOCATION: (1)..(1167)
<223> OTHER INFORMATION: Y stands for T/U or C
<220> FEATURE:
<221> NAME/KEY: unsure
<222> LOCATION: (1)..(1167)
<223> OTHER INFORMATION: V stands for A or G or C

<400> SEQUENCE: 15
ctgtcaaaga aattctcgag gttacatgga tatcttgaga acttaagaaa ttttacagta       60
taattgaaca agtatatgca gcatatccta atttctggac tgactggtag ccataaactg      120
aatttgaatt catagaaatt attggagtag cgtttgagct tctcaaggtc catacaaaga      180
acacattctc aactatccgt ctcataggat acaacatttt caattgcagt tcaacaccaa      240
aaaaatgtaa aaaatagaaa catcatgacc aggtaatcaa acatactcg ttcgatacgg       300 aatctattat tggtacattt aaaaggctag aaaaacaaa cttcagtagc tatctcagca       360
ttataactta ttatgtttcc agcaaaagcc ataacaaatc ttatataact ttcacaaaga      420
```

| | |
|---|---|
| aacaattttt atcatatccc tggacatata atgaacccct tatgtgttca gaactttgcc | 480 |
| cttgaccatg tatttgtgtt gtaaaaaatc cacttattat gtatacataa ttgatttaca | 540 |
| acaacaaaca caatgtaatc ccacaagtgg agtgtggtga ggactttacc cctaccttac | 600 |
| gagatagaga gattgtttct aatagaccct cggctaaagt aaaagcattt caaagcaacg | 660 |
| cgaatataaa gaaggcatga taaaacacta aggaagcat gctagagcat tcttaccgag | 720 |
| gaacaataac tacgacaaga tatataatac aataatcgaa gtacaagaaa cagaaaatag | 780 |
| aataacaaag atcaaataac aaaacaagaa actacccaaa taattccacg actactagta | 840 |
| tgaaaggata agccagacaa cactcaaata cctaactaac cttctacccc tcatccgtgt | 900 |
| cctccataac ctcctagaac actctttcta aatattgtct ytvcccccac ccccctcca | 960 |
| tctctcaatt tttgaatttt atacactcaa ccaccttgca aatttgtcac atgatactta | 1020 |
| catatggctc tacaagtgtc attttcttc catatttgat attataaaaa ataaaataaa | 1080 |
| aaactaagga gatgatccag atatattgga aaatgaaatg caaggctaa aaataattga | 1140 |
| aattaacatg aaattagtaa aaattac | 1167 |

<210> SEQ ID NO: 16
<211> LENGTH: 321
<212> TYPE: DNA
<213> ORGANISM: Solanum tuberosum
<220> FEATURE:
<221> NAME/KEY: variation
<222> LOCATION: (1)..(321)
<223> OTHER INFORMATION: M stands for A or C
<220> FEATURE:
<221> NAME/KEY: variation
<222> LOCATION: (1)..(321)
<223> OTHER INFORMATION: V stands for A or G or C

<400> SEQUENCE: 16

| | |
|---|---|
| mmmvgcaagc aatgcaccac agttagttta tatcaaaaag aagaaaggta ttaacggagc | 60 |
| taaaaactgt tatataccac atgaaagaag ttgataatgt gaaaacacca tgctcataaa | 120 |
| gattgtaatt caaataacaa atgcccacag gagtaaagag ctgtctttcc caagttaagg | 180 |
| tattataaat tggcggaacg aagtaacaca tgtttgacat ctccacacgg tgcacagatc | 240 |
| aaatatgcca tgagcaccag tccagaagtt ttccaactat ttatatacta tccatgcaac | 300 |
| catataaatt atcaaacata c | 321 |

<210> SEQ ID NO: 17
<211> LENGTH: 504
<212> TYPE: DNA
<213> ORGANISM: Solanum tuberosum

<400> SEQUENCE: 17

| | |
|---|---|
| ctgcaaaaaa agagagcagt ttacacaaga aaaaactgct aaatctcaac aaaagtatca | 60 |
| tgaatttaat attaaggaag ctatttcgaa cagaaagagt aactcatgat aatagaagga | 120 |
| aattgtgaag caacagaagg aagactttct ttatttctac aaaattgctt taagactata | 180 |
| tttgatgctt gtatagtaca tgttgaatcc cctcagcttc tttatgtcta acttttttt | 240 |
| atatttgaa tctccttagt gaaaatcttt gctttgccac tgacactccg ggggtgtgtc | 300 |
| acttctccaa aaaccttgtc tacttttttg aagacccaat caaacagctt tttaaaagat | 360 |
| caaaaaaatg gccaggtgcc acctaaatgg agccactact tactcccgg tatgcaaaat | 420 |
| tctctagcaa agtcaaagta ggtataaaca attcatcttc caaataagg tcaaactgcc | 480 |
| taaagcacaa cttttggctg ttac | 504 |

<210> SEQ ID NO: 18
<211> LENGTH: 146
<212> TYPE: DNA
<213> ORGANISM: Solanum tuberosum

<400> SEQUENCE: 18

```
ctgcattgtg gatgagttaa ttagaagcat aaccttaata gcaattagaa catgtaagaa      60
agccaatgat gctgcaacat catgctttaa taggaaaatc tgttatgatg atggaaacta    120
ctattttgta gtagacgagg acctac                                         146
```

<210> SEQ ID NO: 19
<211> LENGTH: 218
<212> TYPE: DNA
<213> ORGANISM: Solanum tuberosum

<400> SEQUENCE: 19

```
ctgtttaatt gctgaagtag taagttctca agcacttata gaattgactc attttgttaa     60
gggaaagagt atgggatcaa gtccaaatta gtaaagacac aattattta acttttgcat    120
ttcaaaatgt cttacataac aagactagta agaacatgaa tcgaaatgcc tgtgatgatg   180
gtgttcaaaa ttcagcttca aggtatgaat aacaaaac                           218
```

<210> SEQ ID NO: 20
<211> LENGTH: 198
<212> TYPE: DNA
<213> ORGANISM: Solanum tuberosum

<400> SEQUENCE: 20

```
ctgtatccag cagacataat aggagtgaac ataaaaatgt cactggataa ataacttatc     60
atgatattca gcggctacca atattctgaa ggcccatggc gaaaataagt acttttatac   120
tttcaggacg tatatatttg gattctatct aacaattgtt ctgagaatta tttagttgta   180
gaaataaatt taaaatac                                                 198
```

<210> SEQ ID NO: 21
<211> LENGTH: 208
<212> TYPE: DNA
<213> ORGANISM: Solanum tuberosum

<400> SEQUENCE: 21

```
ctgtggttag aagctaaaag tgaatagatg agaaaaatta cctccaaata gagggatat      60
tgaaaagaa acacaatgca tgaaaagaat aaacaaatga taaacgagaa aattgaataa    120
tccatcagaa ccctggttac ctcacaaaga gtgagatttt ccgtggctaa cctatatgaa   180
ccttaaaatg caatagaaac agacaaac                                      208
```

<210> SEQ ID NO: 22
<211> LENGTH: 293
<212> TYPE: DNA
<213> ORGANISM: Solanum tuberosum

<400> SEQUENCE: 22

```
ctgtacaagt tcatcaaaca tttcacaatt actccaaaac agacacactt gcaaactcta     60
tacagtaatc ttctatacta caaaaaagta acaatgtttt tttttaagat gacatttgtt   120
ctcagcaaca taatagaaat ccctagacaa tggaaacatt catcatgttg ttttcctcta   180
tgtttcaacc cctttgatgt tcaacagttc aggtcatttt gaggaatgaa tcttgttcaa   240
```

```
gtaagccaaa ctaattgtaa ttatcacaaa atatctaaag atgtaagaca tac        293

<210> SEQ ID NO: 23
<211> LENGTH: 376
<212> TYPE: DNA
<213> ORGANISM: Solanum tuberosum

<400> SEQUENCE: 23
ctgcatttca tcatgagggg gaggaaagac ggagaaatat agatatcaga tttagaccat   60
ttcaattagt atcacttcat tgtaaagaaa ggtaagtat ccaacaaata tagcaggctg   120
tggattggta gcctgaaact atagcttcaa agaatcaact taagctgctc atcaaggcct  180
tagtggtaga atgaggcgg taataagtgt aaatgaatct aatacttgga tctcgaaaca   240
aaaatcagaa attcggttgg aaaataagta gaacaagatg aaatgagcta tcatccccag  300
aaccaagtag acttccaagt aagcaatcta aaaattacta gattatttaa caagctgcga  360
ttcaaaatac ttgaac                                                  376

<210> SEQ ID NO: 24
<211> LENGTH: 172
<212> TYPE: DNA
<213> ORGANISM: Solanum tuberosum

<400> SEQUENCE: 24
ctgcaaagtg aagtaactaa tcagtacagc tattaccgaa tttgaccagc tattggatta   60
aataatatga aatccatcat caagaaatgg aaggtaaaaa ggtttctact tgtccttgga  120
tagaattaaa gcacttcata aacccaacac tttcaacttt agatgatttt ac           172

<210> SEQ ID NO: 25
<211> LENGTH: 145
<212> TYPE: DNA
<213> ORGANISM: Solanum tuberosum

<400> SEQUENCE: 25
ctgttttcgt catgcgagga tcagaaaaaa gagttaaatt agacaatgtg aaaatgattt   60
gtttcagtta cttctccata aaacttgttc agtacattaa aaacaagcag agcaataatt  120
tcatggataa gtaaaacata tatac                                        145

<210> SEQ ID NO: 26
<211> LENGTH: 242
<212> TYPE: DNA
<213> ORGANISM: Solanum tuberosum

<400> SEQUENCE: 26
ctgtcatgag aacagattgt atgtcagcat gaagacaaag atcatcaata acagttttc    60
tccttttga attagctaaa caacgcaggg ggagggcagg aggctcaaac acttccgaac   120
tcagacagtc ggatatctta caaactaaa gatggatgag acaattacag ttcttttgg   180
tgagagaact gtaccctaca tctgttatct tattatcaaa agttattcaa gcaaatcctt  240
ac                                                                 242

<210> SEQ ID NO: 27
<211> LENGTH: 797
<212> TYPE: DNA
<213> ORGANISM: Solanum tuberosum

<400> SEQUENCE: 27
cttcacaaac aaggagaaga agaagcaaaa agaaagatga atatagttag cttagttcaa   60
```

-continued

```
tataaaaaat ttctctccaa gctatttttc tgctagcaaa attcattagt tatttaactt    120
ttctatacat aaagctgcac aaagaaatag tagtacattt ttttgacttg cacaaaataa    180
ctgtgttgtc catttctga catgtgttca tctacatgca ctgtttcaac aacaacaact     240
acttcagtcc caaacaagtt gggtcgcttt agctacacat gttgctttca cttctgttac    300 ttcttttttgg acttttttc ttgagccaag ggtctattga aaaaatcctc tctacctctg    360
agataggagt aagttttgca tacactctac cctcccctg aaaccacttt gtgggactac     420
acgaggtatg ttgttgttga tgttagcgca gacaccaaag gtggacatta tatgactatt    480
cctagcttta cttcagggcg gttttaagtt cccatcaact tcattttga tcatttacct     540 aagtttatgc aggtgcaagc tacatgcact ggtttaggga aaagaggat agagaagaat     600 ttttttggca tccttttgtt ttgtaacagt aagatgccaa agtagacct tattacggct     660 attcctacct ttcaaattag tagttcagag gacttaactg gcgattgtgg cggtaatcaa    720
tagttaactt ctatcgcatt caaataacta tgaacaaaac cacaataaaa agggaggtca    780
cacggcaaga actgtac                                                    797
```

<210> SEQ ID NO: 28
<211> LENGTH: 2169
<212> TYPE: DNA
<213> ORGANISM: Solanum tuberosum

<400> SEQUENCE: 28

```
cgaatgggtt ttgataaaac tttgaaatta atttccattg attaaattat ggtactttgc    60
ttcagctgct gccttcttgt atgttctgat tcttgatttc ctcatttag tggcttttta     120 taaaaaaaca ttatgaccct tttgttagtc ctcccctttc tgaatatttc actcagaccc    180
cattagtttc gaaattgaag taaaacatat ttttttttagt attgtagttt ttttatattt    240
ctacttactt actcgttata caatttctat ttaggtaatc taatcgactt tttgtataca     300
taatacatgt attttggta aagagttttt tactttctcc tagtggtaag gcagatatag     360
ttaaggattt attgacctaa tatgaacgcc ataattttta tattttgtat atacgtatat     420
ttaaaagttt actagatatg tataaataag atatttaaaa tttaattata aatacaaatg     480
attatggtaa aattttgacc tccaaattaa atatttaaa atcaagattt gtcactactt     540
atatatatct tgttgtaaat ccctttaat caagttgtga gtttacaaat attcgttggt     600
taggctaaaa aaataagct ataaagatca agtataaaat tatgcatttt ctgcatttaa      660
tttgaaaaaa tatgttggag caatctaaaa ttgtttgttg attataaaat aagtcgtttt     720
ttgtttttaa taattgataa actatttatt ctgcttaaag ttttagaatg tcaaaaaata    780 atttattta atgaccttaa atgattgaat aagatgtaga cacactcaat tacaaagtta     840
caatattaat acacttgtct attgggtcat ggattatatc atctaatata aataacatgt     900
caaattaaag cttcttataa agttcatagg aactaagata aactttgtga atggccaagc    960
atttttcaga acatcatggg tggtatgaca atcaaattga acttatggga tgaaaaatga   1020
atatcattca actaagaggg cacaacttga catgttagaa agtaaagcaa atttagtagt   1080
gggccaaata aaagaaatta atttgtcagt ttattcttaa actttacctt ctttgaactt   1140
ccacgttatc aaaggttcac ggttcatatg aaggccatgt gtatcctttt taattttggt    1200
attccgtgtt caatatcgat taatttaaat tcgcatgaca aaatcctata ttaaagtata    1260
aagtattttc taaaacagac aagttcaata ctttaatttt acactgaatg cataaattta    1320
```

-continued

| | |
|---|---|
| cactataata attccagtcg cagtctacat tacaataatt aacaattta gcatgaaatg | 1380 |
| aaaaacttta aattatatgc catcaaatca cttaaagtat acattttttt aataactagt | 1440 |
| tctaatccca cttgaaatga gagttatttt aatatcgacc gttaattacc attttattat | 1500 |
| taaatctgca actacagtca actacaccaa tgattttgct gatgccaact cataatataa | 1560 |
| tatccaccgt tcatgtgatt aattcaatat ttcatatacg tacgtaacaa aaattactaa | 1620 |
| attaacgttg gatataccat accctaagct ctgccaaatg tcaatgttct atcattagct | 1680 |
| attttatgc atctataata gatgttaaat tcatattcta agattgaact taatcataaa | 1740 |
| ctcaaaattt gtggtacctg tcaatgcctc caaaagttga ttgaacataa acgttaagat | 1800 |
| ctgtgtactt gtcttttcct tgtaataatg tatgtatgat aataataata agagaacaaa | 1860 |
| atatggcaaa ataaacactt ttttaacatg taactcaaaa caagtaatag gcaaaagtac | 1920 |
| agatgacaac acaacactgt aaacatcatt gaggaaaaca aaaaccatac aacattttga | 1980 |
| ctgtaaatga agagtttgaa acaaaaaact atgttcaaac cgacgccaag ctaacgaaaa | 2040 |
| tagccataga gttctaagaa gcagatgcaa cagttccacg ggttagtatc gtctgtagta | 2100 |
| ggaccggtca tgagaactcg aaagaatctg aaaggaagta atgcatttga accagtaatt | 2160 |
| ggccatgat | 2169 |

<210> SEQ ID NO: 29
<211> LENGTH: 11478
<212> TYPE: DNA
<213> ORGANISM: Solanum tuberosum
<220> FEATURE:
<221> NAME/KEY: variation
<222> LOCATION: (1)..(11478)
<223> OTHER INFORMATION: B stands for G or C or T/U
<220> FEATURE:
<221> NAME/KEY: variation
<222> LOCATION: (1)..(11478)
<223> OTHER INFORMATION: R stands for G or A
<220> FEATURE:
<221> NAME/KEY: variation
<222> LOCATION: (1)..(11478)
<223> OTHER INFORMATION: K stands for G or T/U
<220> FEATURE:
<221> NAME/KEY: variation
<222> LOCATION: (1)..(11478)
<223> OTHER INFORMATION: W stands for A or T/U
<220> FEATURE:
<221> NAME/KEY: variation
<222> LOCATION: (1)..(11478)
<223> OTHER INFORMATION: M stands for A or C

<400> SEQUENCE: 29

| | |
|---|---|
| atcatggcca attactggtt caaatgcatt acttcctttc agattctttc gagttctcat | 60 |
| gaccggtcct actacagacg atactaaccc gtggaactgt tgcatctgct tcttagaact | 120 |
| ctatggctat tttcgttagc ttggcgtcgg tttgaacata gttttttgttt tcaaactctt | 180 |
| catttacagt caaaatgttg tatggttttt gttttcctca atgatgttta cagtgttgtg | 240 |
| ttgtcatctg tacttttgcc tattacttgt tttgagttac atgttaaaaa agtgtttatt | 300 |
| ttgccatatt ttgttctctt attattatta tcatacatac attattacaa ggaaaagaca | 360 |
| agtacacaga tcttaacgtt tatgttcaat caacttttgg aggcattgac aggtaccaca | 420 |
| aattttgagt ttatgattaa gttcaatctt agaatatgaa tttaacatct attatagatg | 480 |
| cataaaaata gctaatgata gaacattgac atttggcaga gcttagggta tggtatatcc | 540 |
| aacgttaatt tagtaatttt tgttacgtac gtatatgaaa tattgaatta atcacatgaa | 600 |
| cggtggatat tatattatga gttggcatca gcaaaatcat tggtgtagtt gactgtagtt | 660 |

```
gcagatttaa taataaaatg gtaattaacg gtcgatatta aataactct catttcaagt    720 gggattagaa ctagttatta aaaaaatgta tactttaagt gatttgatgg catataattt    780 aaagttttc  atttcatgct aaaattgtta attattgtaa tgtagactgc gactggaatt    840
attatagtgt aaatttatgc attcagtgta aaattaaagt attgaacttg tctgttttag    900
aaaatacttt atactttaat ataggatttt gtcatgcgaa tttaaattaa tcgatattga    960
acacggaata ccaaaattaa aaaggataca catggccttc atatgaaccg tgaacctttg   1020
ataacgtgga agttcaaaga aggtaaagtt taagaataaa ctgacaaatt aatttctttt   1080
atttggccca ctactaaatt tgctttactt tctaacatgt caagttgtgc cctcttagtt   1140
gaatgatatt cattttcat  cccataagtt caatttgatt gtcataccac ccatgatgtt   1200
ctgaaaaatg cttggccatt cacaaagttt atcttagttc ctatgaactt tataagaagc   1260
tttaatttga catgttattt atattagatg atataatcca tgacccaata gacaagtgta   1320
ttaatattgt aactttgtaa ttgagtgtgt ctacatctta ttcaatcatt taaggtcatt   1380
aaaataaatt attttttgac attctaaaac tttaagcaga ataaatagtt tatcaattat   1440
taaaaacaaa aaacgactta tttataaatc aacaaacaat tttagattgc tccaacatat   1500
ttttccaaat taaatgcaga aaatgcataa ttttatactt gatctttata gcttattttt   1560
tttagcctaa ccaacgaata tttgtaaact cacaacttga ttaaaaggga tttacaacaa   1620
gatatatata agtagtgaca aatcttgatt ttaaatattt taatttggag gtcaaaattt   1680
taccataatc atttgtattt ataattaaat tttaaatatc ttatttatac atatctagta   1740
aactttaaaa tatacgtata tacaaaaatat aaaattattg gcgttcatat taggtcaata  1800
aatccttaac tatatctgcc ttaccactag gagaaagtaa aaaactcttt accaaaaata   1860
catgtattat gtatacaaaa agtcgattag attacctaaa tagaaattgt ataacgagta   1920
agtaagtaga aatataaaaa aactacaata ctaaaaaaaa tatgttttac ttcaatttcg   1980
aaactaatgg ggtctgagtg aaatattcag aaagggaggg actaacaaaa gggtcataat   2040
gtttttttat aaaaagccac taaaatgagg aaatcaagaa tcagaacata caagaaggca   2100
gcagctgaag caaagtacca taatttaatc aatggaaatt aatttcaaag ttttatcaaa   2160
acccattcga ggatcttttc catctttctc acctaaagtt tcttcagggg taattttta   2220 taatttcatg ttaatttcaa ttattttag  cctttgcatt tcattttcca atatatctgg   2280
atcatctcct tagttttta  ttttattttt tataatatca aatatggaag aaaaatgaca   2340
cttgtagagc catatgtaag tatcatgtga caaatttgca aggtggttga gtgtataaaa   2400
ttcaaaaatt gagagatgga ggggggggtgg gggbaragac aatatttaga aagagtgttc   2460
taggaggtta tggaggacac ggatgagggg tagaaggtta gttaggtatt tgagtgttgt   2520
ctggcttatc ctttcatact agtagtcgtg gaattatttg ggtagtttct tgttttgtta   2580
tttgatcttt gttattctat tttctgtttc ttgtacttcg attattgtat tatatatctt   2640
gtcgtagtta ttgttcctcg gtaagaatgc tctagcatgc ttcctttagt gttttatcat   2700
gccttcttta tattcgcgtt gctttgaaat gcttttactt tagccgaggg tctattagaa   2760
acaatctctc tatctcgtaa ggtaggggta aagtcctcac cacactccac ttgtgggatt   2820
acattgtgtt tgttgttgta aatcaattat gtatacataa aagtggatt ttttacaaca   2880 caaatacatg gtcaagggca aagttctgaa cacataaagg gttcattata tgtccaggga   2940
tatgataaaa attgtttctt tgtgaaagtt atataagatt tgttatggct tttgctggaa   3000
```

```
acataataag ttataatgct gagatagcta ctgaagtttg ttttttctag ccttttaaat    3060
gtaccaataa tagattccgt atcgaacgag tatgttttga ttacctggtc atgatgtttc    3120
tattttttac atttttttgg tgttgaactg caattgaaaa tgttgtatcc tatgagacgg    3180
atagttgaga atgtgttctt tgtatggacc ttgagaagct caaacgctac tccaataatt    3240
tctatgaatt caaattcagt ttatggctac cagtcagtcc agaaattagg atatgctgca    3300
tatacttgtt caattatact gtaaaatttc ttaagttctc aagatatcca tgtaacctcg    3360
agaatttctt tgacaggctt ctagaaataa gatatgtttt ccttctcaac atagtactgg    3420
actgaagttt ggatctcagg aacggtcttg ggatatttct tccaccccaa aatcaagagt    3480
tagaaaagat gaaagggtat gtttgataat ttatatggtt gcatggatag tatataaata    3540
gttggaaaac ttctggactg gtgctcatgg catatttgat ctgtgcaccg tgtggagatg    3600
tcaaacatgt gttacttcgt tccgccaatt tataatacct taacttggga agacagctc    3660
tttactcctg tgggcatttg ttatttgaat tacaatcttt atgagcatgg tgttttcaca    3720
ttatcaactt ctttcatgtg gtatataaca gttttttagct ccgttaatac ctttcttctt    3780
tttgatataa actaactgtg gtgcattgct tgcbkkkatg aagcacagtt cagctatttc    3840
cgctgttttg accgatgacg acaattcgac aatggcaccc ctagaggaag atgtcaagac    3900
tgaaaatatt ggcctcctaa atttggatcc aactttggaa ccttatctag atcacttcag    3960
acacagaatg aagagatatg tggatcagaa aatgctcatt gaaaaatatg agggacccct    4020
tgaggaattt gctcaaggta acagccaaaa gttgtgcttt aggcagtttg accttatttt    4080
ggaagatgaa ttgtttatac ctactttgac tttgctagag aattttgcat accggggagt    4140
aagtagtggc tccatttagg tggcacctgg ccatttttt gatcttttaa aaagctgttt    4200
gattgggtct tcaaaaaagt agacaaggtt tttggagaag tgacacaccc ccggagtgtc    4260
agtggcaaag caaagatttt cactaaggag attcaaaata taaaaaaagt atagacataa    4320
agaagctgag gggattcaac atgtactata caagcatcaa atatagtctt aaagcaattt    4380
tgtagaaata aagaaagtct tccttctgtt gcttcacaat ttccttctat tatcatgagt    4440
tactctttct gttcgaaata gcttccttaa tattaaattc atgatacttt tgttgagatt    4500
tagcagtttt ttcttgtgta aactgctctc ttttttttgca ggttatttaa aatttggatt    4560
caacagggaa gatggttgca tagtctatcg tgaatgggct cctgctgctc agtaggtcct    4620
cgtctactac aaaatagtag tttccatcat cataacagat tttcctatta aagcatgatg    4680
ttgcagcatc attggctttc ttacatgttc taattgctat taaggttatg cttctaatta    4740
actcatccac aatgcaggga agcagaagtt attggcgatt tcaatggatg gaacggttct    4800
aaccacatga tggagaagga ccagtttggt gtttggagta ttagaattcc tgatgttgac    4860
agtaagccag tcattccaca caactccaga gttaagtttc gtttcaaaca tggtaatgga    4920
gtgtgggtag atcgtatccc tgcttggata agtatgcca ctgcagacgc cacaaagttt    4980
gcagcaccat atgatggtgt ctactgggac ccaccacctt cagaaaggtt ttgttattca    5040
taccttgaag ctgaattttg aacaccatca tcacaggcat ttcgattcat gttcttacta    5100
gtcttgttat gtaagacatt ttgaaatgca aagttaaaa taattgtgtc tttactaatt    5160
tggacttgat cccatactct ttcccttaac aaaatgagtc aattctataa gtgcttgaga    5220
acttactact tcagcaatta aacaggtacc acttcaaata ccctcgccct cccaaacccc    5280
gagccccacg aatctatgaa gcacatgtcg gcatgagcag ctctgagcca cgtgtaaatt    5340
cgtatcgtga gtttgcagat gatgttttac ctcggattaa ggcaaataac tataatactg    5400
```

```
tccagttgat ggccataatg gaacattctt actatggatc atttggatat catgttacaa   5460
acttttttgc tgtgagcagt agatatggaa acccggagga cctaaagtat ctgatagata   5520
aagcacatag cttgggttta caggttctgg tggatgtagt tcacagtcat gcaagcaata   5580
atgtcactga tggcctcaat ggctttgata ttggccaagg ttctcaagaa tcctactttc   5640
atgctggaga gcgagggtac cataagttgt gggatagcag gctgttcaac tatgccaatt   5700
gggaggttct tcgtttcctt ctttccaact tgaggtggtg gctagaagag tataactttg   5760
acggatttcg atttgatgga ataacttcta tgctgtatgt tcatcatgga atcaatatgg   5820
gatttacagg aaactataat gagtatttca gcgaggctac agatgttgat gctgtggtct   5880
atttaatgtt ggccaataat ctgattcaca agattttccc agatgcaact gttattgccg   5940
aagatgtttc tggtatgccg ggccttggcc ggcctgtttc tgagggagga attggttttg   6000
tttaccgcct ggcaatggca atcccagata agtggataga ttatttaaag aataagaatg   6060
atgaagattg gtccatgaag gaagtaacat cgagtttgac aaataggaga tatacagaga   6120
agtgtatagc atatgcggag acccatgatc aggtatttta aatttatttc tacaactaaa   6180
taattctcag aacaattgtt agatagaatc caaatatata cgtcctgaaa gtataaaagt   6240
acttattttc gccatgggcc ttcagaatat tggtagccgc tgaatatcat gataagttat   6300
ttatccagtg acatttttat gttcactcct attatgtctg ctggatacag tctattgttg   6360
gtgacaagac cattgcattt ctcctaatgg acaaagagat gtattctggc atgtcttgct   6420
tgacagatgc ttctcctgtt gttgatcgag gaattgcgct tcacaaggtt tgtctgtttc   6480
tattgcattt taaggttcat ataggttagc cacggaaaat ctcactcttt gtgaggtaac   6540
cagggttctg atgattatt caattttctc gtttatcatt tgtttattct tttcatgcat    6600
tgtgtttctt tttcaatatc cctcttattt ggagtaatt tttctcatct attcactttt    6660
agcttctaac cacagatgat ccattttttc acaatggcct tgggaggaga ggggtacctc   6720
aatttcatgg gtaacgaggt atgtcttaca tctttagata ttttgtgata attacaatta   6780
gtttggctta cttgaacaag attcattcct caaaatgacc tgaactgttg aacatcaaag   6840
gggttgaaac atagaggaaa acaacatgat gaatgtttcc attgtctagg gatttctatt   6900
atgttgctga gaacaaatgt catcttaaaa aaaacattgt ttactttttt gtagtataga   6960
agattactgt atagagtttg caagtgtgtc tgttttggag taattgtgaa atgtttgatg   7020
aacttgtaca gtttggccat cctgagtgga ttgacttccc tagagagggc aataattgga   7080
gttatgacaa atgtagacgc cagtggaacc tcgcggatag cgaacacttg agatacaagg   7140
ttcaagtatt ttgaatcgca gcttgttaaa taatctagta atttttagat tgcttacttg   7200
gaagtctact tggttctggg gatgatagct catttcatct tgttctactt attttccaac   7260
cgaatttctg attttttgttt cgagatccaa gtattagatt catttacact tattaccgcc   7320
tcatttctac cactaaggcc ttgatgagca gcttaagttg attctttgaa gctatagttt   7380
caggctacca atccacagcc tgctatattt gttggatact tacctttct ttacaatgaa    7440 gtgatactaa ttgaaatggt ctaaatctga tatctatatt tctccgtctt tcctcccct    7500 catgatgaaa tgcagtttat gaatgcattt gatagagcta tgaattcgct cgatgaaaag   7560
ttctcattcc tcgcatcagg aaaacagata gtaagcagca tggatgatga taataaggta   7620
aaatcatcta aagttgaaag tgttgggttt atgaagtgct ttaattctat ccaaggacaa   7680
gtagaaacct ttttaccttc catttcttga tgatggattt catattattt aatccaatag   7740
```

-continued

```
ctggtcaaat tcggtaatag ctgtactgat tagttacttc actttgcagg ttgttgtgtt    7800
tgaacgtggt gacctggtat ttgtattcaa cttccaccca agaacacat  acgaagggta    7860
tatatgtttt acttatccat gaaattattg ctctgcttgt ttttaatgta ctgaacaagt    7920
tttatggaga agtaactgaa acaaatcatt ttcacattgt ctaatttaac tcttttttct    7980
gatcctcgca tgacgaaaac aggtataaag ttggatgtga cttgccaggg aagtacagag    8040
ttgcactgga cagtgatgct tgggaatttg gtggccatgg aagagtaagg atttgcttga    8100
ataacttttg ataataagat aacagatgta gggtacagtt ctctcaccaa aaagaactgt    8160
aattgtctca tccatcttta gttgtataag atatccgact gtctgagttc ggaagtgttt    8220
gagcctcctg ccctccccct gcgttgttta gctaattcaa aaaggagaaa actgtttatt    8280
gatgatcttt gtcttcatgc tgacatacaa tctgttctca tgacagactg gtcatgatgt    8340
tgaccatttc acatcaccag aaggaatacc tggagttcca gaaacaaatt tcaatggtcg    8400
tccaaattcc ttcaaagtgc tgtctcctgc gcgaacatgt gtggtacagt tcttgccgtg    8460
tgacctccct ttttattgtg gttttgttca tagttatttg aatgcgatag aagttaacta    8520
ttgattaccg ccacaatcgc cagttaagtc ctctgaacta ctaatttgaa aggtaggaat    8580
agccgtaata aggtctactt ttggcatctt actgttacaa acaaaagga tgccaaaaaa    8640
attcttctct atcctctttt tccctaaacc agtgcatgta gcttgcacct gcataaactt    8700
aggtaaatga tcaaaaatga agttgatggg aacttaaaac cgccctgaag taaagctagg    8760
aatagtcata taatgtccac ctttggtgtc tgcgctaaca tcaacaacaa catacctcgt    8820
gtagtcccac aaagtggttt caggggggagg gtagagtgta tgcaaaactt actcctatct    8880
cagaggtaga gaggattttt tcaatagacc cttggctcaa gaaaaaaagt ccaaaaagaa    8940
gtaacagaag tgaaagcaac atgtgtagct aaagcgaccc aacttgtttg ggactgaagt    9000
agttgttgtt gttgaaacag tgcatgtaga tgaacacatg tcagaaaatg gacaacacag    9060
ttattttgtg caagtcaaaa aaatgtacta ctatttcttt gtgcagcttt atgtatagaa    9120
aagttaaata actaatgaat tttgctagca gaaaatagc  ttggagagaa attttttata    9180
ttgaactaag ctaactatat tcatcttcct ttttgcttct tcttctcctt gtttgtgaag    9240
gcttattaca gagttgatga acgcatgtca gaaactgaag attaccagac agacatttgt    9300
agtgagctac taccaacagc caatatcgag gagagtgacg agaaacttaa agattcgtta    9360
tctacaaata tcagtaacat tgacgaacgc atgtcagaaa ctgaagttta ccagacagac    9420
atttctagtg agctactacc aacagccaat attgaggaga gtgacgagaa acttaaagat    9480
tcgttatcta caaatatcag taacattgat cagactgttg tagtttctgt tgaggagaga    9540
gacaaggaac ttaaagattc accgtctgta agcatcatta gtgatgttgt tccagctgaa    9600
tgggatgatt cagatgcaaa cgtctggggt gaggactagt cagatgattg atcgacccta    9660
ctaccgattg gtgatcgcta tccttgctct ctgagaaata ggtgaggcga aacaaaaaaa    9720
aatttgcatg ataaaaagtc tgattttatg atcgctatcc tcgctctctg agaaagaagc    9780
gaaacaaagg cgactcctgg actcgaatct ataagataac aaaggcgact cctgggactc    9840
gaatctataa gataacaaag gcaattccaa gacttgaatc tataaaaaat ttagttaaga    9900
atgattaacg tccgatccta attcgaatcg aggcatctta ccactccatt gataattata    9960
taagtcaata agtcatataa wagtattaaa aactaaattg acttgatcgg tctatcaaaa   10020
atmagatmaa attgtgttca tatgtaacat ttttgttgtc acaattagct taattacatc   10080
tttcatgtgc aataacaaag aaatgatagg aatttagaga ttccaatttt tttgttgcca   10140
```

```
caattaactt aattacatct ttcatttgca ataacaaaga aatgatagga atttagagat    10200
ccagtgtcaa tacacaacct aggccaacat cgaaagcata actgtaaact catgcatgaa    10260
gaaatcagtc gtaaaaatga ataaatgcga cataaaaaca aattgcatgt atcattaatg    10320
tgacttaact acaagtaaaa ataaatttaa caaatgtaac ttaactacaa gtaaaaataa    10380
attgcttcta tcattaacaa acaaacagaa ttaaaaagaa aaaaacatac taaatcttac    10440
cgtcattcga taaaaaaaaa taccaaattc ataatgcaag gaaaacgaaa cgcgtcctga    10500
tcgggtatca acgatgaaat ggaccagttg gatcgactgc ctgcacaacg ttaggtatgc    10560
caaaaaaaag aacacgatcc tttgcacccg ttcgatgatt atcagtatgt tcacaaaaaa    10620
aacttaagtt catcccagtg tacaacagcc ccaacatctg ccccaagtaa caaaaaacaa    10680
ccaatttatc ttattcttat ctgccacaaa ataatcggtt tcacactatt ctcttgttat    10740
acaaaattga caagtaggaa ggagaggagt catccaaata aacggtgcac gttctttgag    10800
aaaagtctta tttttcgtaa gatccaattt caacaaactt ttcttcaagt caaaattcct    10860
gatagtgtat ctcctctcga cgacctcttg cattgaacga tctccgctta tcatgaaaag    10920
ttgcttggat aacaagtatt gcaaggggg gacagtagct attaagttag tcggcccaag    10980
gaaatggagg agtgatagtc tcgaatatta ttcacctctt tagcattacc cggtctggct    11040
ttaaggagtt acgtctttta cgctcgccaa tttcttttt tagaatggtt ggtgtcaaaa    11100
tcgcgagttg tggaaggttc aagttactcg attcgtgatt ttcaagtatg agtggtgaga    11160
gagattcgat attttcacga ggtgtattcg aggtctagta gaacgaaggg tgtcactaat    11220
gaaagtttca agagttcatc atcatcttct tctagtagat tttcgctttc aaatgagtat    11280
gaaaattctt cctcttttct attgattttc ttcattgttt tcttcattgt tgtggttgtt    11340
attgaaaaga aagaaaattt ataacagaaa aagatgtcaa aaaaaaggta aaatgaaaga    11400
gtatcatata cttaaagagt tgcgtagaga taagtcaaaa gaaacagaat tatagtaatt    11460
tcagctaagt tagaattc                                                 11478
```

<210> SEQ ID NO: 30
<211> LENGTH: 26
<212> TYPE: DNA
<213> ORGANISM: Solanum tuberosum

<400> SEQUENCE: 30
ggaattccag tcgcagtcta cattac                                        26

<210> SEQ ID NO: 31
<211> LENGTH: 28
<212> TYPE: DNA
<213> ORGANISM: Solanum tuberosum

<400> SEQUENCE: 31
cgggatccag aggcattaag atttctgg                                      28

<210> SEQ ID NO: 32
<211> LENGTH: 32
<212> TYPE: DNA
<213> ORGANISM: Solanum tuberosum

<400> SEQUENCE: 32
cgggatccaa agaaattctc gaggttacat gg                                 32

<210> SEQ ID NO: 33

-continued

```
<211> LENGTH: 32
<212> TYPE: DNA
<213> ORGANISM: Solanum tuberosum

<400> SEQUENCE: 33
cgggatccgg ggtaattttt actaatttca tg                              32

<210> SEQ ID NO: 34
<211> LENGTH: 28
<212> TYPE: DNA
<213> ORGANISM: Solanum tuberosum

<400> SEQUENCE: 34
ccatcgatac tttaagtgat ttgatggc                                   28

<210> SEQ ID NO: 35
<211> LENGTH: 28
<212> TYPE: DNA
<213> ORGANISM: Solanum tuberosum

<400> SEQUENCE: 35
cgggatcctg ttctgattct tgatttcc                                   28
```